(12) United States Patent
Rau et al.

(10) Patent No.: US 11,565,036 B2
(45) Date of Patent: Jan. 31, 2023

(54) ASSEMBLY NEST FOR A PEN INJECTION DEVICE WITH LOCKING FUNCTION

(71) Applicant: Sanofi-Aventis Deutschland GMBH, Frankfurt am Main (DE)

(72) Inventors: Matthias Rau, Rüsselsheim (DE); Winfried Huthmacher, Rüsselsheim (DE); Sebastian Braun, Rüsselsheim (DE); Marc Schader, Frankfurt am Main (DE); Markus Janiak, Frankfurt am Main (DE); Michael Kneip, Frankfurt am Main (DE); Martin Baumeyer, Rüsselsheim (DE); Peter Nober, Rüsselsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 667 days.

(21) Appl. No.: 16/483,626

(22) PCT Filed: Feb. 6, 2018

(86) PCT No.: PCT/EP2018/052973
§ 371 (c)(1),
(2) Date: Aug. 5, 2019

(87) PCT Pub. No.: WO2018/141993
PCT Pub. Date: Aug. 9, 2018

(65) Prior Publication Data
US 2020/0093981 A1 Mar. 26, 2020

(30) Foreign Application Priority Data
Feb. 6, 2017 (EP) .................................. 17154738

(51) Int. Cl.
*B65G 47/26* (2006.01)
*B65G 47/52* (2006.01)
*F16B 21/06* (2006.01)
(Continued)

(52) U.S. Cl.
CPC .......... *A61M 5/008* (2013.01); *A61M 5/3202* (2013.01); *A61M 5/344* (2013.01);
(Continued)

(58) Field of Classification Search
None
See application file for complete search history.

(56) References Cited

U.S. PATENT DOCUMENTS 3,899,095 A * 8/1975 Wiese .................... B65G 65/23
222/166
4,084,770 A * 4/1978 Warmann ............... B65G 51/28
406/149

(Continued)

FOREIGN PATENT DOCUMENTS

AU 2008262348 12/2008
CN 104619167 5/2015
(Continued)

OTHER PUBLICATIONS

International Preliminary Report on Patentability in International Application No. PCT/EP2018/052973, dated Aug. 6, 2019, 23 pages.
International Search Report and Written Opinion in International Application No. PCT/EP2018/052973, dated Jun. 21, 2018, 28 pages.

*Primary Examiner* — Kavel Singh
(74) *Attorney, Agent, or Firm* — Fish & Richardson P.C.

(57) ABSTRACT

An assembly nest for transporting a tubular sub assembly of a drug delivery device on an automated production line, in which the tubular sub assembly includes a tubular body and a cap that is wider than the tubular body. The assembly nest includes a base against which a sub assembly of a drug delivery device is mountable to orientate said sub assembly in a predetermined position; and locking mechanism having a resilient member to urge the locking mechanism into one
(Continued)

of: an unlocked position, in which a sub assembly of a drug delivery device can be mounted to the base; or a locked position, in which the locking mechanism engages a mounted sub assembly to retain it in its predetermined position on the base.

15 Claims, 21 Drawing Sheets

(51) Int. Cl.
  *A61M 5/00* (2006.01)
  *A61M 5/32* (2006.01)
  *A61M 5/34* (2006.01)
  *A61M 5/31* (2006.01)
  *F16B 21/00* (2006.01)

(52) U.S. Cl.
  CPC ..... *B65G 47/26* (2013.01); *A61M 2005/3104* (2013.01); *A61M 2207/10* (2013.01); *B65G 47/52* (2013.01); *F16B 21/00* (2013.01)

(56) References Cited

U.S. PATENT DOCUMENTS

| | | |
|---|---|---|
| 4,995,870 A | 2/1991 | Baskas |
| 10,391,246 B2 * | 8/2019 | Henderson .......... A61M 5/3129 |
| 2009/0005736 A1 | 1/2009 | Flachbart et al. |
| 2015/0013276 A1 | 1/2015 | Okajima et al. |

FOREIGN PATENT DOCUMENTS

| | | |
|---|---|---|
| EP | 2601992 | 6/2013 |
| JP | H07-124228 | 5/1995 |
| JP | 2005-192947 | 7/2005 |
| JP | 2014-217578 | 11/2014 |
| JP | 2016-523672 | 8/2016 |
| WO | WO 2008/153985 | 12/2008 |
| WO | WO 2014/011539 | 1/2014 |
| WO | WO 2015/004052 | 1/2015 |
| WO | WO 2018/141993 | 8/2018 |

* cited by examiner

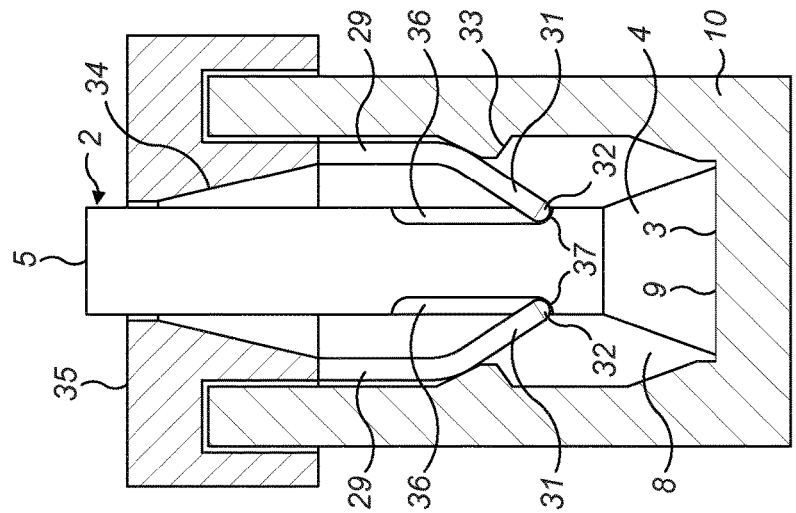
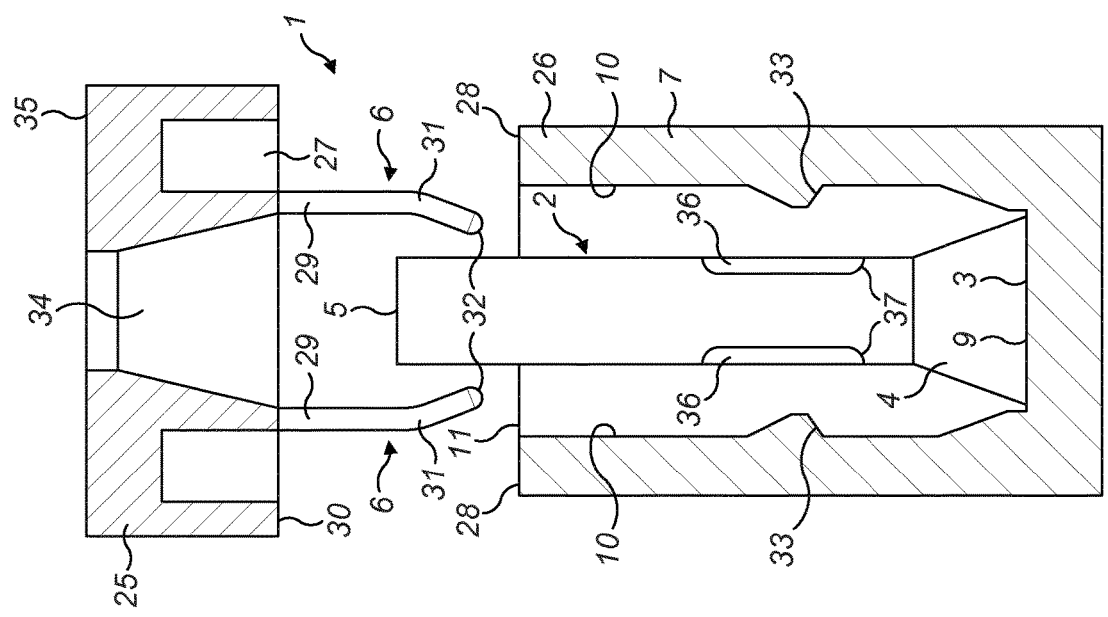

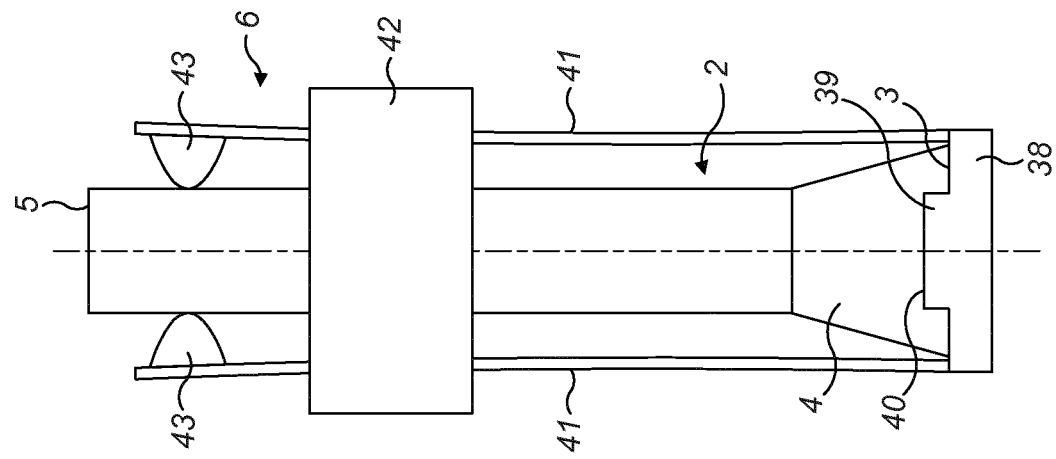
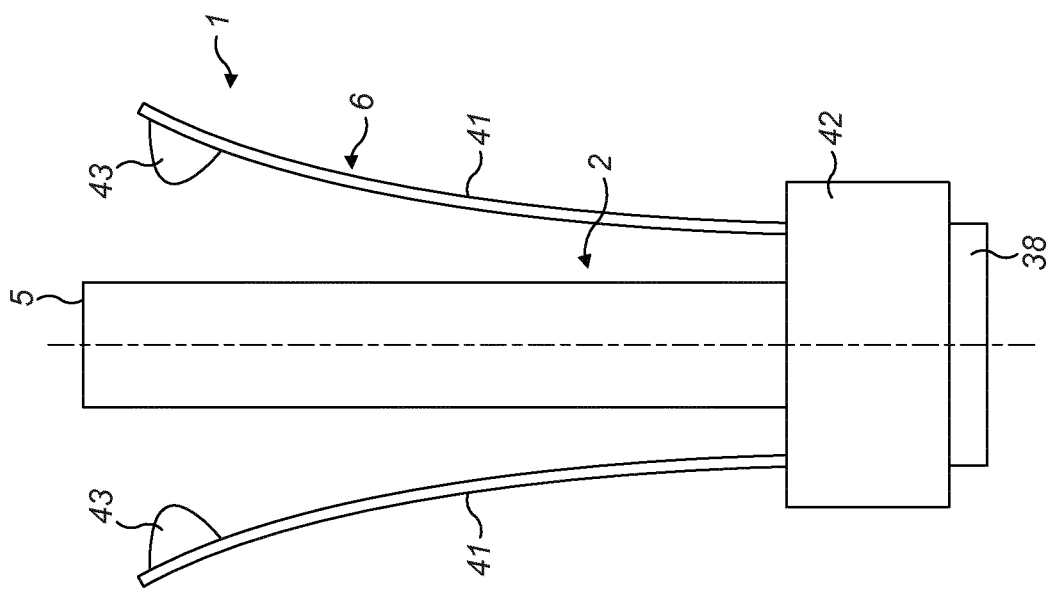

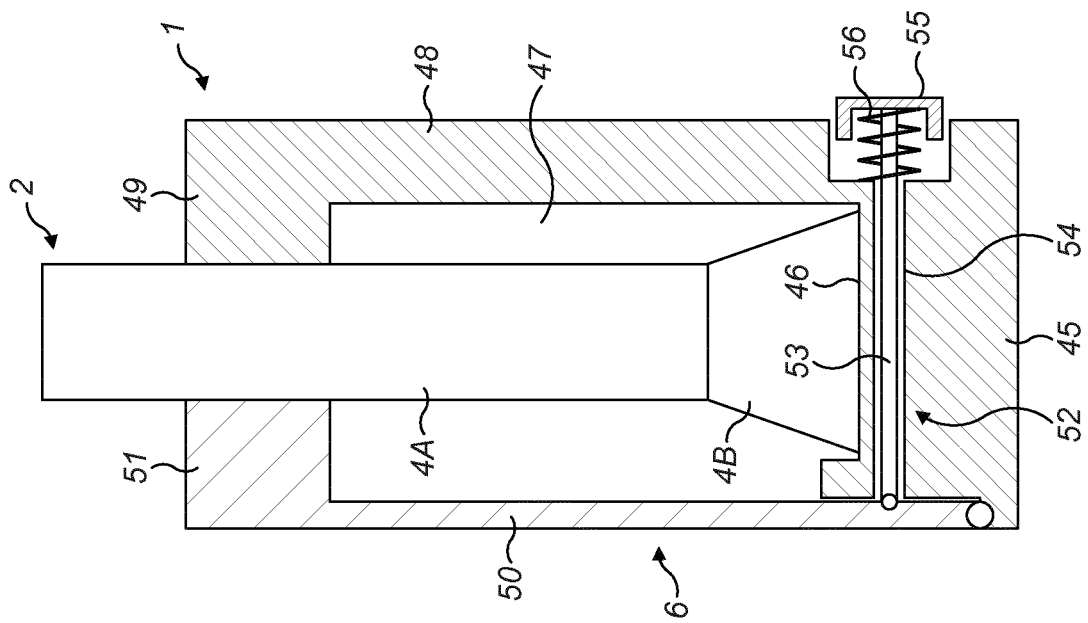
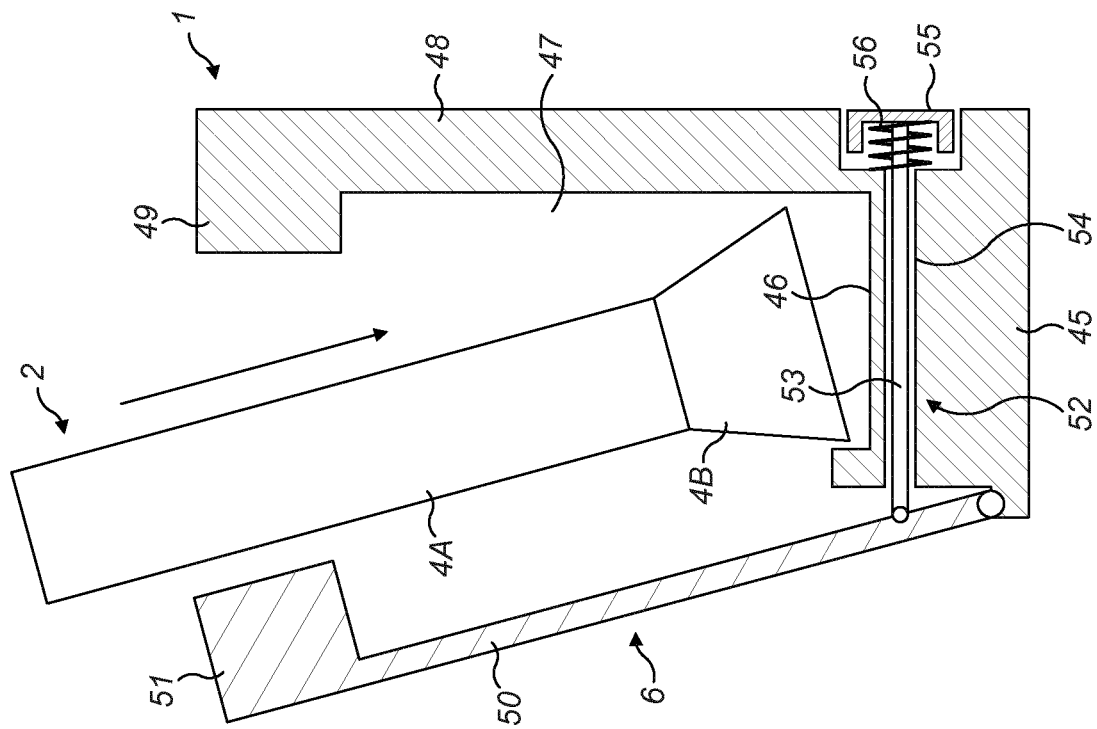
FIG. 7A
FIG. 7B

ASSEMBLY NEST FOR A PEN INJECTION DEVICE WITH LOCKING FUNCTION

CROSS REFERENCE TO RELATED APPLICATIONS

The present application is the national stage entry of International Patent Application No. PCT/EP2018/052973, filed on Feb. 6, 2018, and claims priority to Application No. EP 17154738.3, filed on Feb. 6, 2017, the disclosures of which are incorporated herein by reference.

TECHNICAL FIELD

The present disclosure relates to an assembly nest for transporting sub-assemblies, in particular sub-assemblies of drug delivery devices, such as pen-type injectors on an automatic assembly line.

BACKGROUND

Drug delivery devices allowing for multiple dosing of a required dosage of a liquid medicinal product and further providing administration of such liquid drug to a patient, are as such well-known in the prior art. Generally, such devices have substantially the same purpose as that of an ordinary syringe. Typically, a medicinal product to be administered is provided in a cartridge having a moveable piston or bung mechanically interacting with a piston rod of a drive mechanism of the drug delivery device. By applying thrust to the piston, a certain and pre-defined amount of the medicinal fluid is expelled from the cartridge.

SUMMARY

Manufacturing and final assembling of such drug delivery devices is typically implemented in a mass-production process. In a typical final assembly scenario, two sub-assemblies can have to be assembled with each other. For instance, a first sub-assembly can include a cartridge and the second sub-assembly can include a housing or body adapted to receive the cartridge.

Since the final assembly is typically conducted almost entirely automatically, the subassemblies can have to be provided in a well-defined and ordered way. Hence, the subassemblies can have to be correctly oriented and disposed on a respective support structure, such as an assembly nest.

Embodiments of the present disclosure can address the problems mentioned above and provide an improved assembly nest.

In an aspect of the disclosure there is provided an assembly nest for transporting a tubular sub assembly of a drug delivery device on an automated production line, the assembly nest including:
  a base against which a sub assembly of a drug delivery device is mountable to orientate said sub assembly in a predetermined position; and
  a locking mechanism having a resilient member to urge the locking mechanism into one of:
    an unlocked position, in which a sub assembly of a drug delivery device can be mounted to the base; or
    a locked position, in which the locking mechanism engages a mounted sub assembly to retain it in its predetermined position on the base;
  in which the locking mechanism includes a locking pin having a gripping end that abuts a sub assembly mounted on the base when the locking mechanism is in the locked position and is spaced from said sub assembly when the locking mechanism is in the unlocked position;
  and in which the resilient member is a coil spring arranged about the pin and arranged to urge the gripping end against a sub assembly mounted to the base.

The locking mechanism can include a locking pin having a gripping end that abuts a sub assembly mounted on the base when the locking mechanism is in the locked position and is spaced from said sub assembly when the locking mechanism is in the unlocked position.

The locking pin can extend through a passage in a wall of the assembly nest so that the locking pin can slide relative to the wall to move the locking mechanism into the locked or unlocked position.

The wall can upstand around the base and the locking pin can slide in an oblique direction relative to the wall such that, when the locking mechanism is slid into the locked position, the locking pin slides down toward the base.

The wall can include first and second portions, in which the first portion upstands perpendicularly from the base and the second portion, opposite the first portion, upstands obliquely, so that the spacing between the first and second portions increases with distance from the base, and in which the passage for the locking pin is provided in the first portion.

The wall can instead upstand obliquely from all around the base so that the space enclosed by the wall increases with distance from the base.

The assembly nest can include two symmetrically opposed locking pins.

In an aspect of the disclosure there is provided an assembly nest for transporting a tubular sub assembly of a drug delivery device on an automated production line, the assembly nest including:
  a base against which a sub assembly of a drug delivery device is mountable to orientate said sub assembly in a predetermined position; and
  a locking mechanism having a resilient member to urge the locking mechanism into one of:
    an unlocked position, in which a sub assembly of a drug delivery device can be mounted to the base; or
    a locked position, in which the locking mechanism engages a mounted sub assembly to retain it in its predetermined position on the base;
  in which the assembly nest further includes an upper part and a lower part that are combinable with each other, in which the lower part includes the base, and in which the upper part includes the locking mechanism, the locking mechanism including resilient arms that depend from the upper part and that extend into contact with a sub assembly mounted to the base when the upper and lower parts are combined.

The lower part can include a wall that upstands around the base to define a receiving space into which a sub assembly of a drug delivery device is inserted when the sub assembly is mounted to the base, and in which the wall includes a protrusion that extends into the receiving space and is arranged so as to displace the resilient arms toward a sub assembly mounted to the base when the upper and lower parts are combined.

The upper part can include an opening through which an end of a sub assembly mounted to the base passes when the upper and lower parts are combined such that an inside face of the opening abuts said end of the sub assembly.

In an aspect of the disclosure there is provided an assembly nest for transporting a tubular sub assembly of a drug delivery device on an automated production line, the assembly nest including:

- a base against which a sub assembly of a drug delivery device is mountable to orientate said sub assembly in a predetermined position; and
- a locking mechanism having a resilient member to urge the locking mechanism into one of:
  - an unlocked position, in which a sub assembly of a drug delivery device can be mounted to the base; or
  - a locked position, in which the locking mechanism engages a mounted sub assembly to retain it in its predetermined position on the base;
- in which the locking mechanism includes at least two resilient arms that extend either side of the base and a locking ring positionable over ends of the arms to retain the locking mechanism in the locked position, the arms being arranged so that when the locking mechanism is in the unlocked position the arms extend outward of a vertical projection of the base, the locking mechanism can further include engaging portions that depend from upper edges of the arms and extend into a vertical projection of the base when the locking mechanism is in the locked position.

The locking ring can be slideably arranged around the resilient arms, in which sliding the locking ring along the length of the arms into the locked position causes the arms to move toward each other so as to engage a sub assembly mounted on the base.

In an aspect of the disclosure there is provided an assembly nest for transporting a tubular sub assembly of a drug delivery device on an automated production line, the assembly nest including:

- a base against which a sub assembly of a drug delivery device is mountable to orientate said sub assembly in a predetermined position; and
- a locking mechanism having a resilient member to urge the locking mechanism into one of:
  - an unlocked position, in which a sub assembly of a drug delivery device can be mounted to the base; or
  - a locked position, in which the locking mechanism engages a mounted sub assembly to retain it in its predetermined position on the base;
- the assembly nest further including:
- an elongate receiving space for receiving a tubular sub assembly defined by a vertical projection of the base; and
- a support upstanding perpendicularly from the base having an alignment element at an upper end thereof that projects into the receiving space, such that, when a tubular sub assembly is received in the receiving space, the cap abuts the base and the alignment element abuts the tubular body;
- in which the locking mechanism extends from the base opposite the support and includes a fixation element that projects into the receiving space when the locking element is in the locked position to clamp the tubular body of a tubular sub assembly received therein between the alignment element and the fixation element.

The locking mechanism can be hingedly attached to the base.

A push rod can extend through the base and mechanically couple to the locking mechanism such that movement of the push rod effects movement of the locking mechanism between the locked and unlocked positions.

The resilient member can be a coil spring arranged about the push rod to urge the push rod into a first position in which the locking mechanism is in the locked position.

In an aspect of the disclosure there is provided an assembly nest for transporting a tubular sub assembly of a drug delivery device on an automated production line, in which said tubular sub assembly includes a tubular body and a cap that is wider than the tubular body, the assembly nest including:

- an elongate receiving space for receiving a tubular sub assembly, a base surface and at least two bearing surfaces, in which the elongate receiving space is defined by a vertical projection of the base surface, the bearing surfaces projecting inwardly into the receiving space such that when a tubular sub assembly is received in the receiving space the cap abuts the base surface and the bearing surfaces abut opposing sides of the tubular body, in which the bearing surfaces are spaced apart in a longitudinal direction of the receiving space and in which a recess is provided in the receiving space opposite the lower bearing surface, the recess projecting outwardly of the receiving space.

The upper bearing surface can forms a U shaped collar that extends around a portion of the tubular body of the tubular sub assembly when the tubular sub assembly is received in the receiving space.

The lower bearing surface and the recess can be spaced from the base surface in the longitudinal direction.

In an aspect of the disclosure there is provided an assembly nest for transporting a tubular sub assembly of a drug delivery device on an automated production line, the assembly nest including:

- an elongate receiving space defined by a semi cylindrical wall having a longitudinal opening along one side in which a sub assembly can be inserted to orientate said sub assembly in a predetermined position; and
- a clamp that moves relative to the receiving space between an open position, in which the longitudinal opening is uncovered, and a closed position in which the clamp abuts a sub assembly inserted in the receiving space to secure it therein.

The receiving space can include a base against which an end of the sub assembly is mountable.

The clamp can be attached to the wall of the receiving space by a hinge.

The clamp can include a slider that describes a partial annulus, the slider being disposed in an arcuate track formed in an upper end of the wall of the receiving space, and in which the slider is slideable along the arcuate track between the open and closed positions.

The clamp can instead include a panel that is hinged along one edge to the wall of the receiving space, and in which, in the closed position, the panel extends across the longitudinal opening.

The panel can include a fixation element that extends from an inside face of the panel into contact with a sub assembly received in the receiving space when the panel is in the closed position.

A locking mechanism can be provided to lock the panel in the closed position.

The locking mechanism can include a sprung latch that is arranged to engage a catch when the panel is in the closed position.

The hinge can include a spring loaded mechanism to bias the panel into the open position.

In an aspect of the disclosure there is provided an assembly nest for transporting a tubular sub assembly of a drug delivery device on an automated production line, in which said tubular sub assembly includes a tubular body and a cap that is wider than the tubular body, the assembly nest including:

a mount against which the cap of a sub assembly of a drug delivery device is mountable to orientate said sub assembly in a predetermined position; and a clamping arm that extends upwardly from the mount and is moveable into a locked position in response to displacement of the mount in which a clamping surface of the clamping arm abuts the tubular body of a sub assembly mounted to the mount.

The assembly nest can include two clamping arms, in which the mount includes two individual mounting parts that are each integrally formed with a respective clamping arm, the each of the mounting parts extending from a lower end of said respective clamping arm into overlapping relation, such that, a cap of a sub assembly is simultaneously contactable with both mounting parts to displace them downwards and cause the clamping arms to move towards each other and into contact with the tubular body of a sub assembly mounted on the mount.

The clamping surface of each clamping arm can be disposed on an upper end of the respective clamping arm, opposite the lower end.

The mounting parts can move into alignment when the respective clamping arms are moved into the locked position to form a flat surface on which the cap of a sub assembly is mountable.

The assembly nest can include a receiving space defined by a vertical projection of a base surface of the receiving space, the receiving space including a wall that upstands perpendicularly about the base surface to an upper edge; in which the mount is moveably disposed within the receiving space and in which the clamping arm is hingedly attached to the mount and includes an extended straight edge, the clamping surface being disposed at an upper end of the straight edge and projecting therefrom toward the vertical projection of the base surface, so that, when the mount is moved in a direction toward the base of the receiving space, the straight edge of the clamping arm pivots about the upper edge of the wall to displace the clamping surface towards the tubular body of a sub assembly mounted on the mount and into the locked position.

The assembly nest can further include a compression spring arranged to urge the mount away from the base surface.

The assembly nest according can further include a locking pin that engages the mount to hold the mount against the compression spring when the clamping arm is in the locked position.

The base surface can include an opening to allow the passage of a fluid into the receiving space.

The assembly nest can include a receiving space defined by a vertical projection of a base surface of the receiving space, the receiving space including a support upstanding perpendicularly from one side of the base surface having an alignment element at an upper end thereof that projects inwardly into the vertical projection of the base surface, in which the clamping arm and the mount are integrally formed and hingedly attached to the base surface so as to allow the mount and the clamping arm to move simultaneously into the locked position in which the mount abuts the base surface, in which the clamping arm includes a fixation element that projects inwardly into the vertical projection of the base surface when the clamping arm is in the locked position so that, when the clamping arm and the mount are in the locked position, the tubular body is clamped between the alignment element and the fixation element.

In an aspect of the disclosure there is provided an assembly nest for transporting a tubular sub assembly of a drug delivery device on an automated production line, in which said tubular sub assembly includes a tubular body and a cap that is wider than the tubular body, the assembly nest including:

a base surface against which the cap of a sub assembly of a drug delivery device is mountable to orientate said sub assembly in a predetermined position; and a clamping mechanism to clamp the tubular body of a sub assembly mounted on the base, the clamping mechanism including a clamping surface and a reservoir into which fluid can be pumped to cause the clamping surface to move into contact with the tubular body.

The assembly nest can further include a wall that upstands around the base, in which the reservoir is a flexible membrane attached to an inside face of the wall and the clamping surface is an outer surface of the membrane.

The reservoir can include a cylinder and the clamping surface can be disposed on a piston moveable within the cylinder.

In an aspect of the disclosure there is provided an assembly nest for transporting a tubular sub assembly of a drug delivery device on an automated production line, in which said tubular sub assembly includes a tubular body and a cap that is wider than the tubular body, the assembly nest including:

a base surface against which the cap of a sub assembly of a drug delivery device is mountable to orientate said sub assembly in a predetermined position;

a wall that upstands around the base; and a clamping mechanism to clamp the tubular body of a sub assembly mounted on the base, the clamping mechanism including a clamp disposed in a track formed through an upper end of the wall, the clamp being displaceable along the track in response to a locking collar being placed over the upper end of the wall between an unlocked position, in which it protrudes from an outer surface of the wall, and a locked position in which it protrudes from an inner surface of the wall and into contact with the tubular body of a sub assembly mounted to the base.

The track can includes a leaf spring that projects from an inner face of the track, the leaf spring being adapted to urge the clamp into one of the locked or unlocked positions.

BRIEF DESCRIPTION OF THE FIGURES

So that the present disclosure can be more fully understood, embodiments thereof will now be described with reference to the accompanying drawings in which:

FIG. 3A shows a section view of an assembly nest according to a third embodiment of the disclosure in an unlocked position;

FIG. 3B shows a section view of an assembly nest according to the third embodiment in an unlocked position;

FIG. 4A shows an assembly nest according to a fourth embodiment of the disclosure in an unlocked position;

FIG. 4B shows an assembly nest according to the fourth embodiment in an unlocked position;

FIG. 7A shows a section view of an assembly nest according to a sixth embodiment of the disclosure in an unlocked position;

FIG. 7B shows a section view of an assembly nest according to the sixth embodiment of the disclosure in a locked position;

DETAILED DESCRIPTION

Figure 1A:
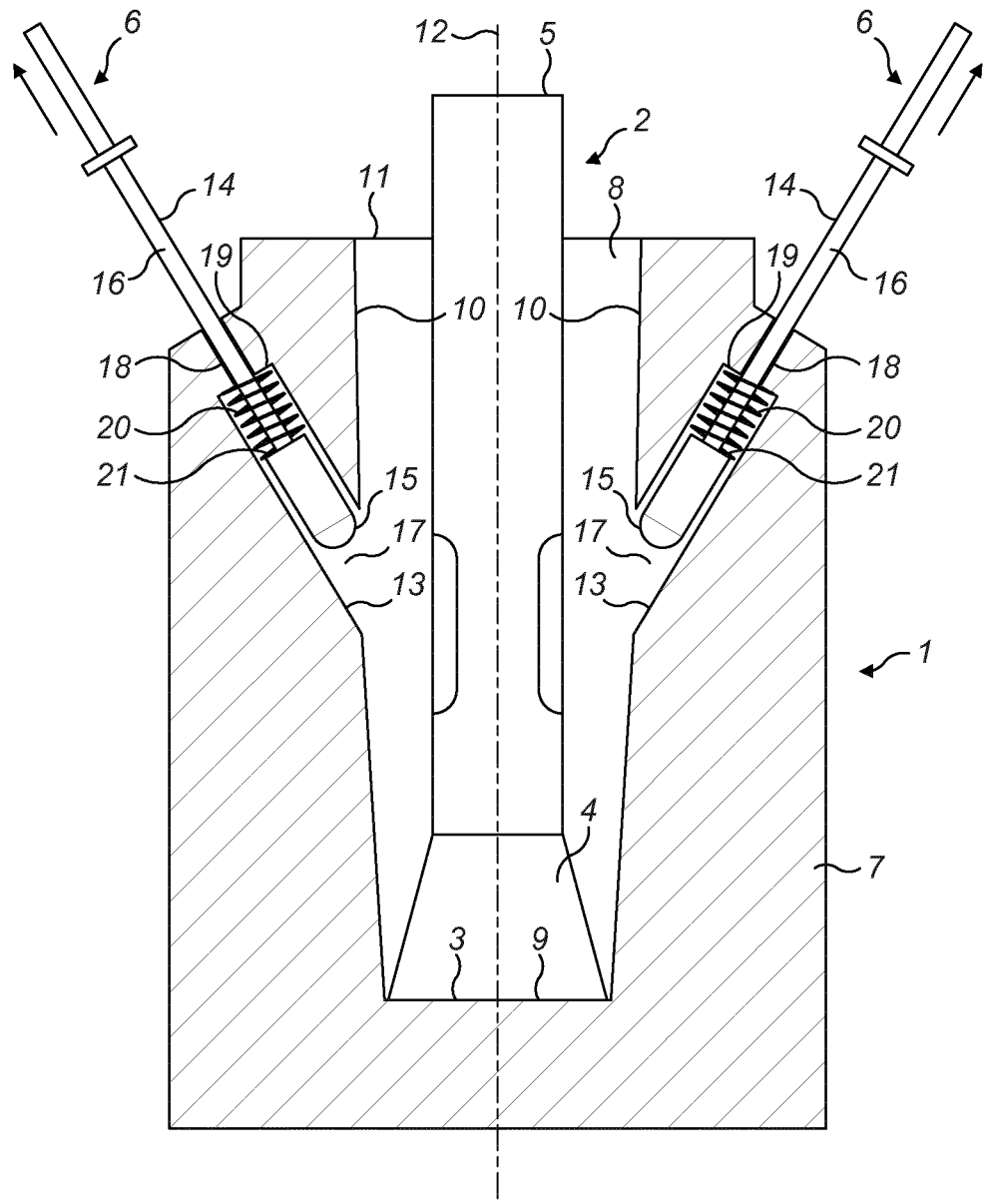
FIG. 1A shows a section view of an assembly nest according to a first embodiment of the disclosure in a locked position.

According to embodiments of the disclosure an assembly nest 1 is provided for holding a sub assembly 2 of a drug delivery device in a predetermined position during an assembly process on an automated assembly line. In the illustrated embodiments, the sub assembly 2 includes an elongate tubular body 4A having an open proximal end 5 and a cap 4B fitted to a distal end 3 of the tubular body 4A. The cap 4B has a diameter which is greater than that of the tubular body 4A.

During an assembly stage of the drug delivery device, a second sub assembly such as a medicament cartridge can be inserted in through the open proximal end 5 of the tubular body 4A. Therefore it is important that the sub assembly 2 is held securely in an upright position with the open proximal end 5 facing upwards.

According to some embodiments of the disclosure, an assembly nest 1 is provided including a locking mechanism 6. The locking mechanism 6 is moveable between a locked position in which the sub assembly 2 is held in the assembly nest 1 and an unlocked position in which the sub assembly 2 can be freely inserted or removed from the assembly nest 1. The locking mechanism 6 includes a resilient member to urge the locking mechanism 6 into either the locked position or the unlocked position. The resilient member eliminates the requirement for actuation in one direction of movement of the locking mechanism 6 from the locked position to unlocked position, or vice versa, thereby simplifying the construction of the assembly nest 1.

Figure 1B:
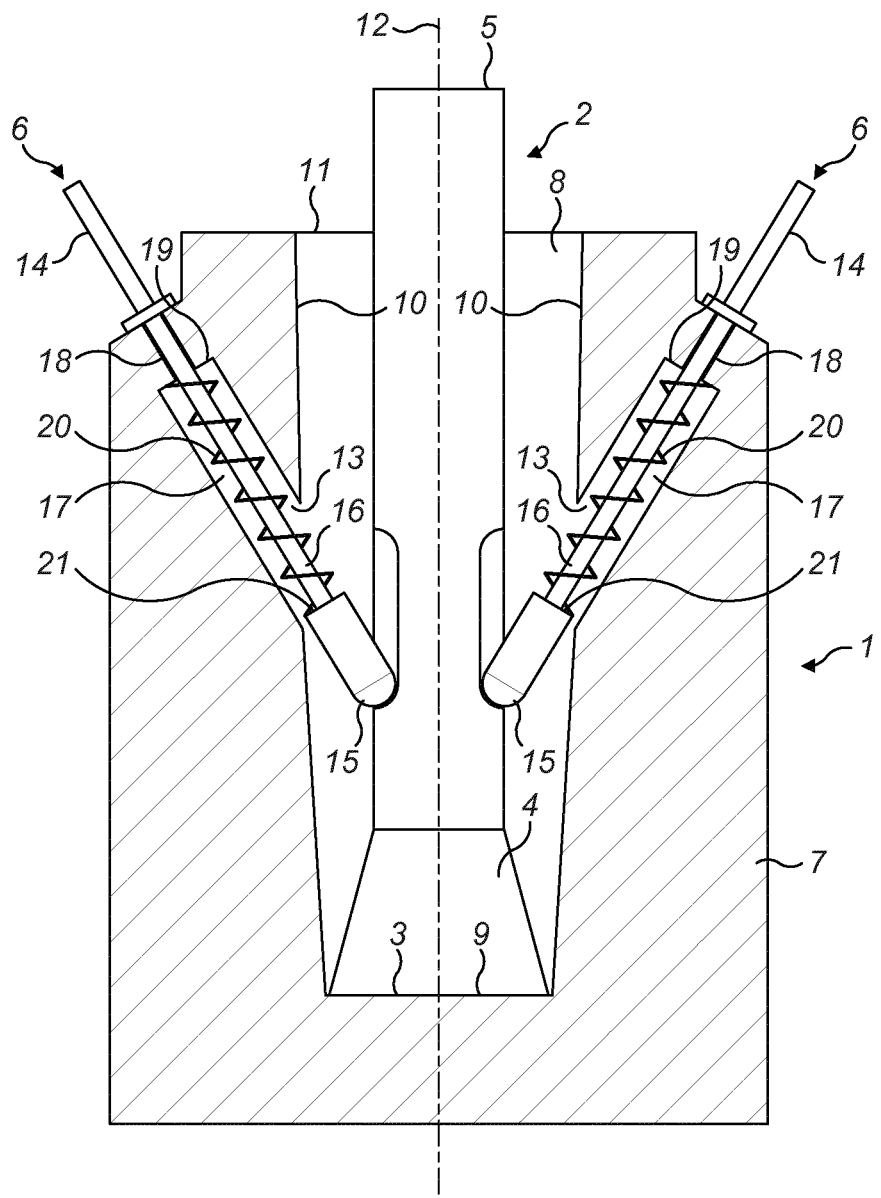
FIG. 1B shows a section view of an assembly nest according to the first embodiment in an unlocked position.

A first embodiment of the disclosure is shown in FIGS. 1A and 1B. In this embodiment the assembly nest 1 includes a nest body 7 having a receiving space 8 in which the sub assembly 2 of the drug delivery device can be inserted in an upright position. The receiving space 8 is an elongate passage that extends into the body 7 to a base 9 disposed in a lower end of the body 7. Walls 10 of the passage taper from an opening 11, through which the sub assembly 2 can be inserted, to the base 9 on which the cap 4B of the sub assembly 2 rests when it is received therein. When the sub assembly 2 is located in the receiving space 8 prior to an assembly stage of the drug delivery device, the cap 4B abuts both the base 9 and the walls 10 to securely locate the cap 4B such that it can only move upwards in a direction along its axis 12, that is, the cap 4B of the sub assembly 2 is prevented from moving in a non-axial direction.

Herein the term axial direction refers to a direction of movement of the sub assembly 2 that corresponds to the direction of its axis 12 and non-axial direction is any direction of movement that is not in the direction of its axis 12.

Two opposing passages 13 extend at an oblique angle through the walls 10 and into the receiving space 8 to accommodate respective resilient locking mechanisms 6 for locking the sub assembly 2 in the receiving space 8 when it is located therein. Each passage 13 extends downwards, that is, toward the base 9 of the receiving space 8.

In this embodiment, each locking mechanism 6 includes locking pins 14 each having a gripping end 15, which is configured to abut the tubular body 4A of the sub assembly 2 received in the receiving space 8, and a shaft 16 which extends from the gripping end 15 through respective passages 13 and out of the body 7.

Each passage 13 is formed of two parts. A first part 17 of a first diameter extends from the receiving space 8 into the body 7. A second part 18 of a second diameter which is less than the first diameter extends axially from the first part 17 so that a shoulder 19 is formed in the passage 13 between the first and second parts 17, 18. The second diameter is substantially equal to the diameter of the shaft 16 of each pin 14 to act as a guide for axial movement of the pins 14 from an unlocked position, in which the gripping ends 15 are withdrawn into the first part 17 of the passage, and a locked position in which the gripping ends 15 are moved into abutting relation with a sub assembly 2 received in the receiving space 8. FIG. 1A illustrates the locked position and FIG. 1B illustrates the unlocked position.

In this embodiment, the resilient member includes a compression coil spring 20 provided to urge the locking pins 14 into the locked position. Each coil spring 20 extends along the shaft 16 of respective locking pins. A first end of each coil spring 20 abuts a first reaction surface 21 provided on the gripping ends 15 of the locking pins 14. A second end of each coil spring 20 abuts the shoulder 19 of respective passages 13 which serve as a second reaction surface 19.

Actuators (not shown) withdraw the locking pins 14 against the force of the compression spring 20 into the unlocked position to facilitate insertion or removal of a sub assembly 2 into the receiving space 8. Each actuator is mechanically coupled to the shaft 16 of a respective locking pin 14 where it protrudes from the body 7.

In operation of the assembly nest 1, the actuators act to withdraw each locking pin 14 against the force of respective compression springs 20 so that the locking pins 14 move along respective passages 13, moving the gripping ends 15 up and into the first part 17 of each passage 13, in which position the locking pins 14 are in the unlocked position. Thereupon, the sub assembly 2 of a drug delivery device is inserted cap 4B first into the receiving space 8 so that the cap 4B abuts the base 9, whereupon the actuators release the force acting to withdraw the locking pins 14 so that they move under the force of respective compression springs 20 to abut the tubular body 4A of the sub assembly 2, in which position the locking pins are in the locked position. The force of the compression springs 20 holds the sub assembly 2 in the assembly nest 1 by friction between the tubular body 4A of the sub assembly 2 and the gripping ends 15 of the locking pins 14 to prevent the sub assembly 2 moving in an axial or non-axial direction. Therefore the sub assembly 2 is fully constrained in an upright position. With the sub assembly 2 of the drug delivery device so installed in the assembly nest 1, the assembly nest 1 can be moved along an automated assembly line (not shown) and an assembly stage performed on the sub assembly 2, such as inserting a second sub assembly.

Figure 2A:
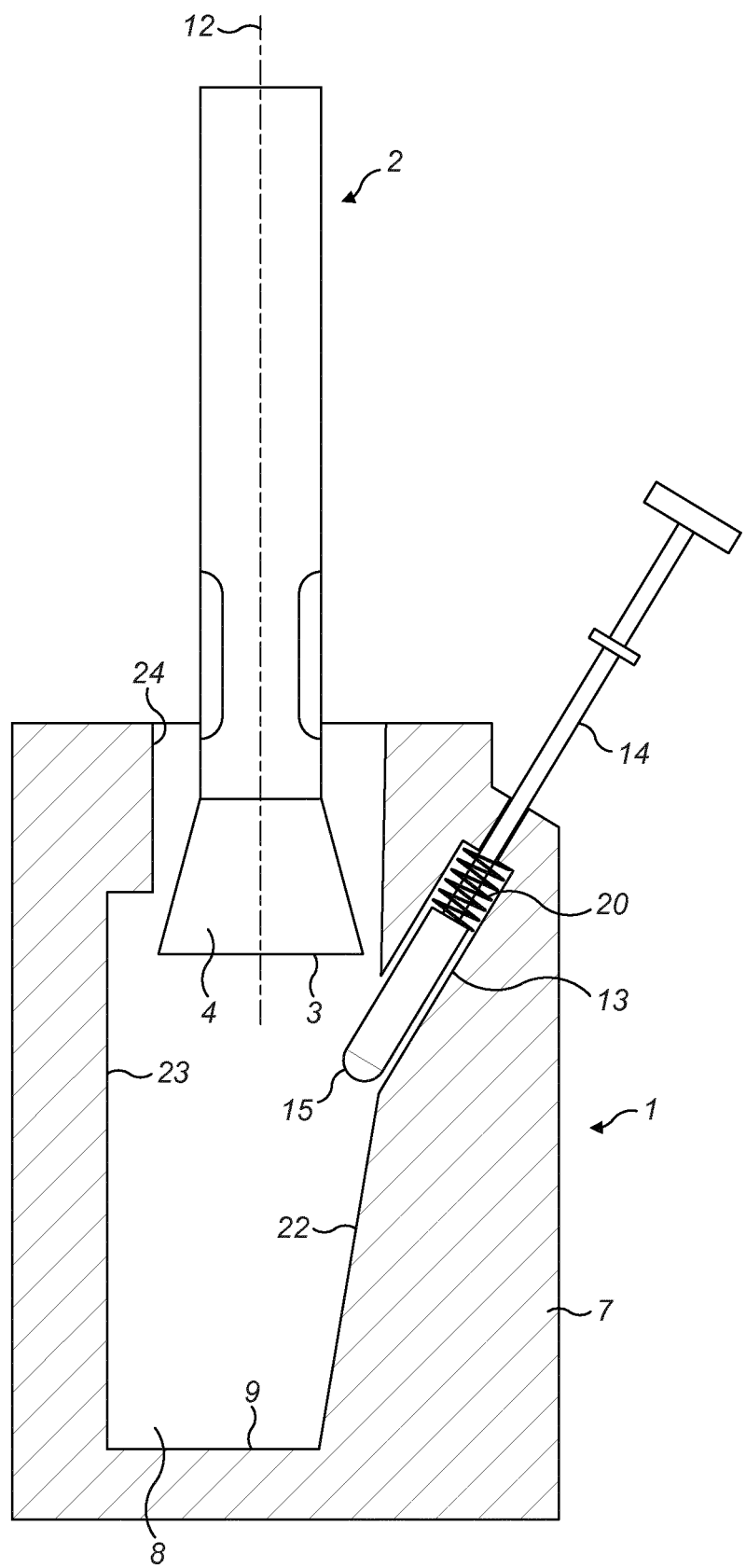
FIG. 2A shows a section view of an assembly nest according to a second embodiment of the disclosure in an unlocked position.
Figure 2B:
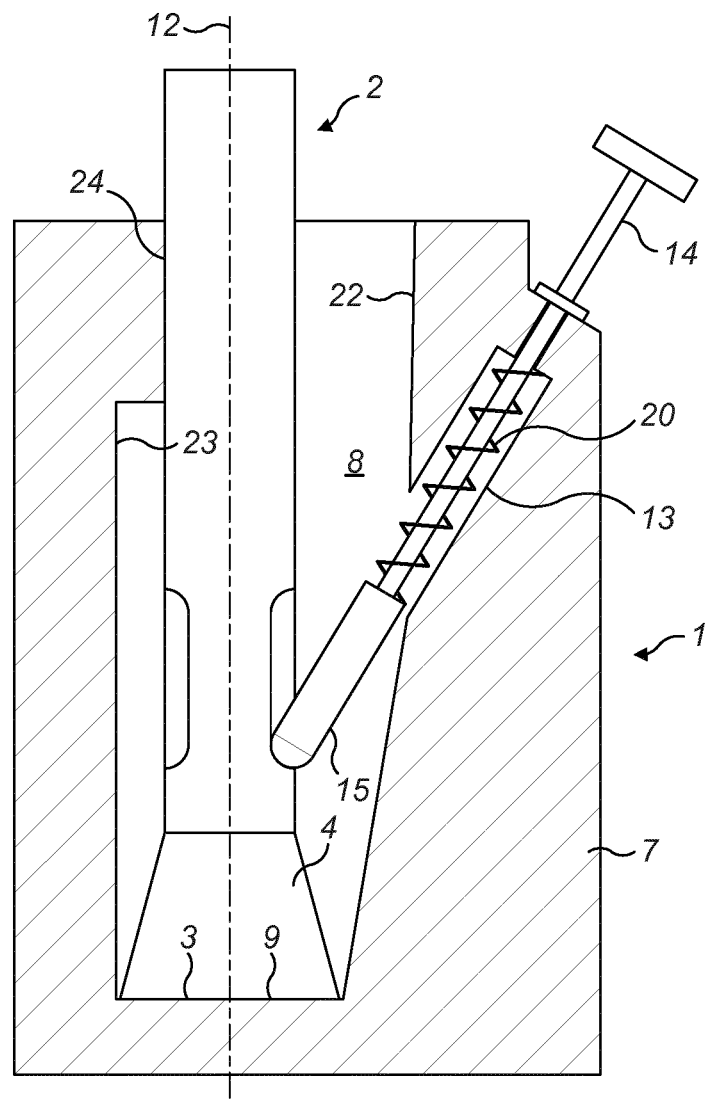
FIG. 2B shows a section view of an assembly nest according to the second embodiment in an unlocked position.

In a second embodiment of the disclosure shown in FIGS. 2A and 2B, in which like features retain the same reference numbers, the assembly nest 1 includes a single passage 13 and a single locking pin 14 extending through the passage 13. In this embodiment the wall 10 that upstands about the base 9 to form the receiving space 8 has a first portion 23 that upstands perpendicular to the base 9 and a second portion 22, opposite the first portion 23, that upstands oblique to the base 9 so that the first 23 and second portions 22 of the wall 10 taper outward from each other. The passage 13 extends through the second portion 22 of the wall.

When the sub assembly 2 is received in the receiving space the cap 4B abuts both the base 9 and the wall 10, where the wall 10 meets the base 9, to securely locate the cap 4 such that it can only move upwards in a direction along its axis 12, that is, the cap 4 is prevented from moving in a non-axial direction.

As shown, the cap 4B tapers outwards from the tubular body 4A so that the cap 4B has an end which is wider than the tubular body 4A. Therefore, when the sub assembly 2 is received in the receiving space 8, the tubular body 4A is spaced from the wall 10 due to the additional width of the cap 4B. A part 24 of the first portion 23 of the wall 10 projects into the receiving space 8 so that when the cap 4B is located against the base 9, the projecting part 24 bridges the space between the tubular body 4A and the first portion 23 of wall 10 and abuts the tubular body 4A to further locate the sub assembly 2 it in an upright position.

With the sub assembly 2 received in the receiving space 8 and with the locking pin 14 disposed in the locked position, as shown in FIG. 2B, the force of the compression 20 spring holds the sub assembly 2 in the assembly nest 1 by friction between the tubular body 4A of the sub assembly 2 and the gripping end 15 of the locking pin 14. Any upwards movement of the sub assembly 2 must be in the direction of the sub assembly's 2 axis 12 due to the constraint of the perpendicular first portion 23 of wall 10. It shall be understood that were the first portion 23 tapered, the sub assembly 2 could be prematurely dislocated from the assembly nest 1 as an upwards movement would also allow it to move outwards and away from the single locking pin 14.

A third embodiment of the disclosure is shown in FIGS. 3A and 3B, in which like features retain the same reference numbers. In this embodiment the body 7 is split into two separable parts: an upper part 25 and a lower part 26. The lower part 26 includes the receiving space 8 and the upper part 25 is configured to attach to the lower part 26 across the opening 11 of the receiving space 8.

The upper part 25 includes a groove 27 into which upper edges 28 of the walls 10 of the lower part 26 are insertable to cause the upper 25 and lower parts 26 to be combined.

In this embodiment the locking mechanism 6 includes the upper part 25 and resilient arms 29 that depend from a lower face 30 of the upper part 25. The resilient arms 29 are arranged so that they are inserted into the receiving space 8 as the upper and lower parts 25, 26 are combined. Each arm 29 is provided with a bent section 31 so that a portion of each arm 29 is angled in towards the opposing arm 29. The arms 29 are spaced apart such that tips 32 of the arms 29 are spaced from a sub assembly 2 received in the receiving space 8 when the upper part 25 is initially combined with the lower part 26.

A protrusion 33 projects into the receiving space 8 from an inside face of the walls 10 of the lower part 26 and is configured to displace the arms 29 inwards as the upper and lower parts 25, 26 are combined, such that the tips 32 of the arms 29 move into engagement with the tubular body 4A of a sub assembly 2 received in the receiving space 8.

The upper part 25 further includes an opening 34 that extends between lower and upper faces 30, 35 of the upper part 25. The opening 34 tapers so that the opening 34 at the lower face 30 of the upper part 25 is larger than the opening 34 at the upper face 35 of the upper part 25. The width of the opening 34 at the upper face 35 is substantially equal to the width of the proximate end 5 of the sub assembly 2. Therefore, when the sub assembly 2 is received in the receiving space 8 and the upper and lower parts 25, 26 are combined, the opening 34 in the upper face 35 of the upper part 25 abuts the proximate end 5 of the tubular body 4A to more securely locate the sub assembly 2 in an upright position.

In operation of the assembly nest 1 of the third embodiment, the upper and lower parts 25, 26 are initially separated in an unlocked position. The sub assembly 2 of a drug delivery device is inserted into the receiving space 8 so that the cap 4B rests on the base 9. The walls 10 are closely spaced to the cap 4 to constrain it in a non-axial direction, as shown in FIG. 3A. Thereupon, the upper and lower parts 25, 26 are recombined into a locked position in which the resilient arms 29 engage the tubular body 4A of the sub assembly 2 to prevent the sub assembly 2 moving in an axial direction by frictional engagement of the tips 32 of the arms 29. With the upper and lower parts 25, 26 combined in the locked position, the opening 34 in the upper part 25 abuts the proximate end 5 of the sub assembly 2 so that the proximate end 5 of the sub assembly 2 is prevented from moving in a non-axial direction. Thus, the sub assembly 2 is fully constrained in an upright position as shown in FIG. 3B.

In the illustrated embodiment, the tubular body 4A of the sub assembly 2 includes grooves 36 that are arranged so that the tips 32 of the arms 29 locate within the grooves 36 and against a lower edge 37 of the grooves 36 when the sub assembly 2 is received in the receiving space 8 and the upper and lower parts 25, 26 are combined. This further constrains the sub assembly 2 in the axial direction.

In a fourth embodiment of the disclosure shown in FIGS. 4A and 4B, in which like features retain the same reference numbers. As seen in FIG. 4B, the base 38 includes a raised portion 39, herein referred to as a tongue 39, which mates with a corresponding groove 40 in a bottom face of the cap 4B. The mating of the tongue 39 and the groove 40 locates the cap 4B of the sub assembly 2 in anon-axial direction.

In this embodiment the locking mechanism 6 includes two resilient arms 41 that extend from the base 38 in an upwards direction and a locking ring 42. The arms 41 can be, for example, spring steel strips. The arms 41 are pre-stressed to bend slightly outwards to allow the sub assembly 2 to be inserted into the assembly nest 1.

The locking ring 42 is disposed around the arms 41. The internal diameter of the locking ring 42 is substantially equal to the spacing between the arms 41 where they attach to the base 38. The locking ring 42 is configured to move along the length of the arms 41. Movement of the locking ring 42 upwards from an unlocked position, adjacent the base 38, to a second locked position above the base 38 displaces the arms 41 inward so that each arm 41 moves towards the opposing arm 41. The force of the arms 41 pressing outwards against the locking ring 42 ensures that the locking ring 42 remains in the locked position without any additional retaining force. The unlocked position is shown in FIG. 4A and the locked position is shown in FIG. 4B.

Tips of the arms 41 are provided with an engaging portion 43, each facing the opposing arm 41. The engaging portion 43 is configured to engage with the tubular body 4A of the sub assembly 2 when it is received in the assembly nest 1 and the locking ring 42 is disposed in the locked position.

In operation, the locking ring 42 is initially disposed in the unlocked position adjacent the base 38 so that the arms 41 are bent outwards to allow the sub assembly 2 to be placed in the assembly nest 1. The sub assembly 2 is placed on the base 38 cap 4B down to effect mating of the tongue 39 and groove 40 and to prevent the cap 4B from moving in a non-axial direction. The locking ring 42 is then moved upward into the locked position to displace the arms 41 inward and bring the engaging portions 43 into engagement with the tubular body 4A of the sub assembly 2. The engaging portions 43 grip the tubular body 4A to prevent the sub assembly 2 moving in an axial direction by frictional engagement of the engaging portions 43 with the sub assembly 2. With the locking ring 42 in the locked position, the tubular body 4A is also prevented from moving in a non-axial direction. Therefore the sub assembly 2 is fully constrained in an upright position.

Figure 5B:
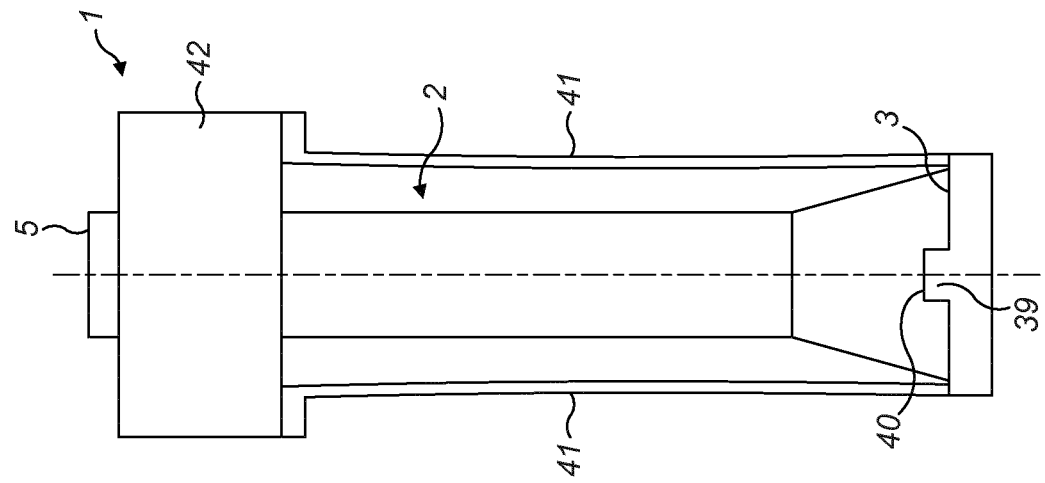
FIG. 5B shows an assembly nest according to the fifth embodiment in an unlocked position.
Figure 5A:
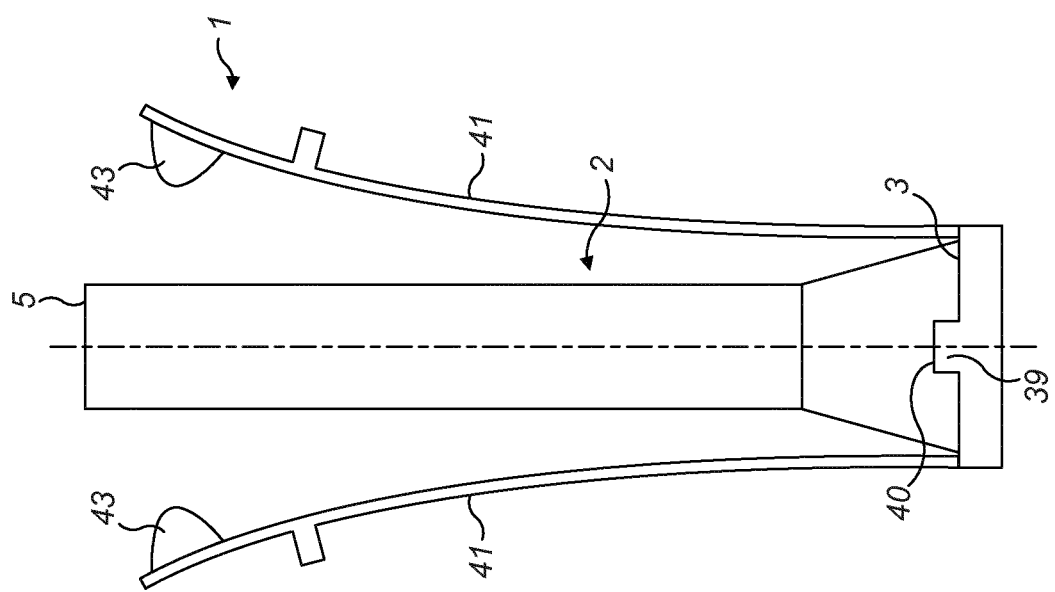
FIG. 5A shows an assembly nest according to a fifth embodiment of the disclosure in an unlocked position.

A fifth embodiment of the disclosure is shown in FIGS. 5A and 5B, in which like features retain the same reference numbers. In this embodiment the assembly nest 1 is similar in construction to the fourth embodiment, however in operation the locking ring 42 is initially removed from the assembly nest 1 and the arms 41 are moved inward by an alternative means. Specifically, the arms are moved from an unlocked position, in which the arms 41 bend slightly outwards to allow a sub assembly 2 to be inserted into the assembly nest 1, to a locked position in which the arms 41 are displaced inward so that each arm 41 is moved toward the opposing arm 41. The arms 41 are moved by, for example, an actuator, although the arms 41 could also be moved by a human operator. When the arms 41 are moved into the locked position, the locking ring 42 is placed over the end of the arms 41 to retain the arms 41 in the locked position. The unlocked position is shown in FIG. 5A and the locked position is shown in FIG. 5B.

In operation, a sub assembly 2 of a drug delivery device is placed on the base 38 cap 4B down to effect mating of the tongue and groove 39, 40 and to prevent the cap 4B of the sub assembly 2 from moving in a non-axial direction. The arms 41 are then displaced by an actuator or human operator to cause the arms 41 to move inward into the locked position whereupon the engaging portions 43 move into engagement with the tubular body 4A of the sub assembly 2. The locking ring 42 is then placed over the end of the arms 41 to prevent the arms 41 from returning to the unlocked position. The engaging portions 43 grip the tubular body 4A to prevent the sub assembly 2 moving in an axial direction by frictional engagement of the engaging portions 43 with the tubular body 4A. With the arms 41 disposed in the locked position and the locking ring 42 placed over the ends of the arms 41, the tubular body 4A is also prevented from moving in a non-axial direction. Therefore the sub assembly 2 is fully constrained in an upright position.

Figure 6:
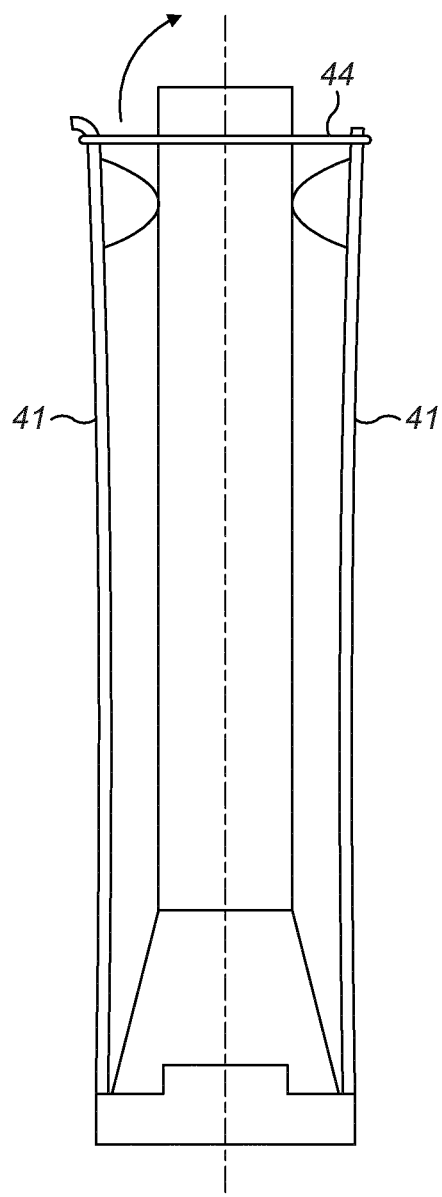
FIG. 6 shows an assembly nest according to a sixth embodiment of the disclosure in a locked position.

It shall be appreciated that other means of holding the arms 41 together in a locked position are envisaged, for example, in the embodiment shown in FIG. 6 the locking ring is omitted and a hinged latch 44 is provided. The latch 44 is hinged to the end of one of the arms 41 and latches to the end of the opposing arm 41 when the arms are in the locked position.

A sixth embodiment of the disclosure is shown in FIGS. 7A and 7B. The assembly nest 1 of the sixth embodiment includes a base 45 having an upper surface 46 on which the cap 4B of the sub assembly 2 is mountable to orient it in the predetermined position. A receiving space 47 for the sub assembly 2 is defined by a vertical projection of the upper surface 46, so that when the sub assembly 2 is mounted to the base 45 it is disposed within the receiving space 47.

A support 48 upstands perpendicularly from the upper surface 46 of the base 45 and includes an alignment element 49 which projects from an upper end of the support 48 into the receiving space 47 and into contact with the tubular body 4A of a sub assembly 2 mounted to the upper surface 46.

The locking mechanism 6 includes an arm 50 that hinges from an opposing side of the base 45 to the support 48. The arm 50 includes a fixation element 51 which projects from an upper end of the arm 50. When the locking mechanism 6 is in the locked position (as shown in FIG. 7B), the arm 50 is arranged perpendicular to the base surface 46 so that the fixation element 51 abuts the tubular body 4A of a sub assembly 2 mounted to the upper surface 46 of the base 45 to clamp the tubular body 4A between the fixation element 51 and the alignment element 49.

When the locking mechanism 6 is in the unlocked position (as shown in FIG. 7A), the arm 50 extends at an angle from the upper surface 46 of the base 45 so that the fixation element 51 is disposed outside of the receiving space 47. Therefore, the space between the fixation element 51 and the alignment element 49 is increased to allow the cap 4B of the subassembly to be inserted down into the receiving space 47 from above the assembly nest 1.

In use, an operator inserts the sub assembly 2 into the receiving space 47 from above and moves the sub assembly 2 down into the predetermined position in which the cap 4B abuts the upper surface 46 of the base 45, whereupon the arm 50 is moved so that fixation element 51 clamps the tubular body 4A to the alignment element 49.

It shall be appreciated that the term "operator" as used herein encompasses both human operation or automated operation and should not be construed as being limited to either.

Also shown in FIGS. 7A and 7B is a mechanism 52 for moving the locking mechanism 6 into the unlocked position. The mechanism 52 includes a push rod 53 located in a channel 54 formed in the base 45 beneath the upper surface 46. A button 55 is provided at one end of the push rod 53, the other end of the push rod 53 being connected to the arm 50, so that, by applying a force to the button 55 in an axial direction of the push rod 53, the push rod 53 is moved along the channel 54 to displace the arm 50 away from the receiving space 47.

In such embodiments the resilient member includes a compression spring 56 disposed between the base 45 and the button 55 so as to urge the button 55 outwards from the base 45 to cause the arm 50 to move toward the receiving space 47.

Figure 8A:
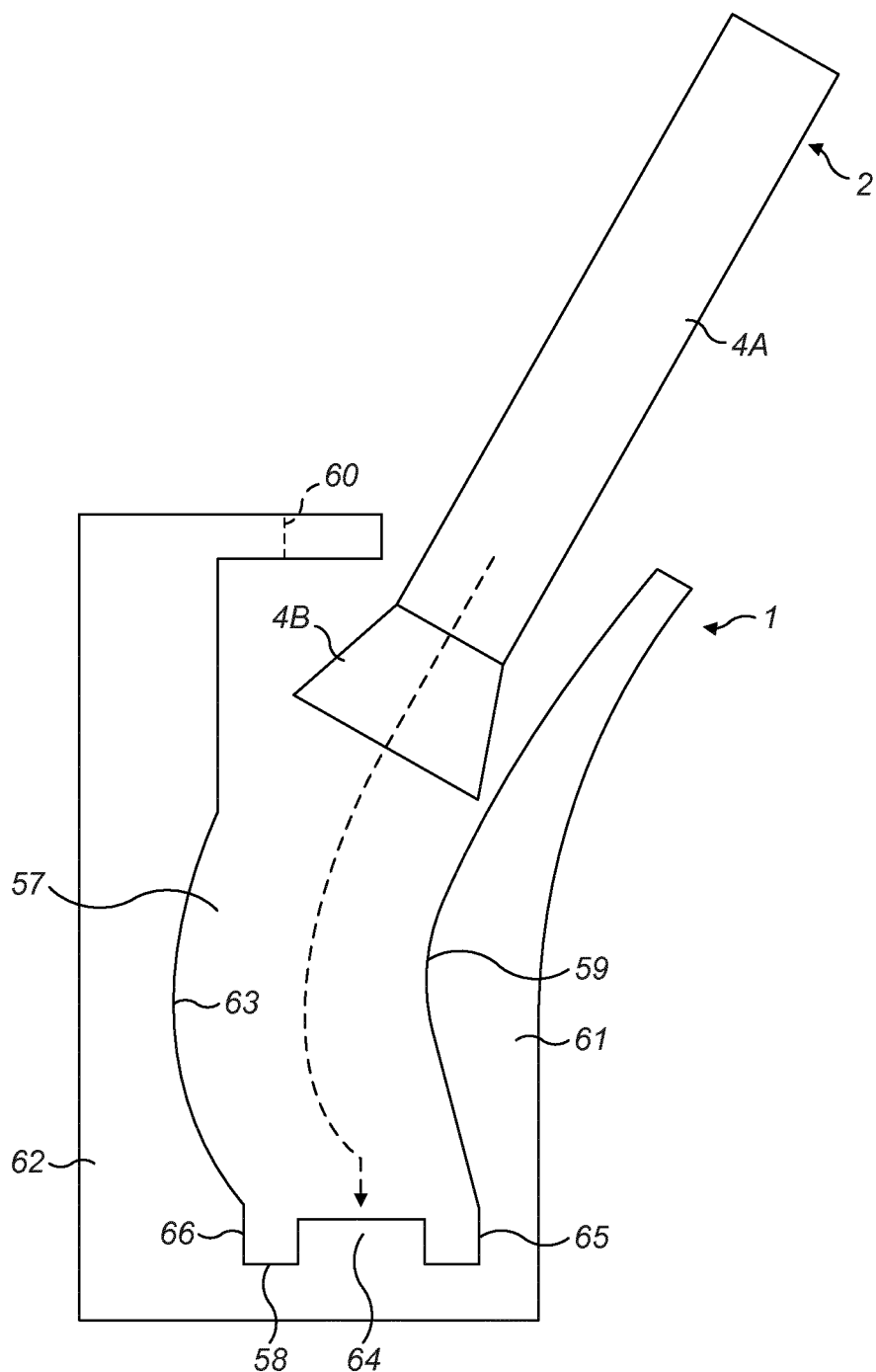
FIG. 8A shows an assembly nest according to an seventh embodiment of the disclosure.
Figure 8B:
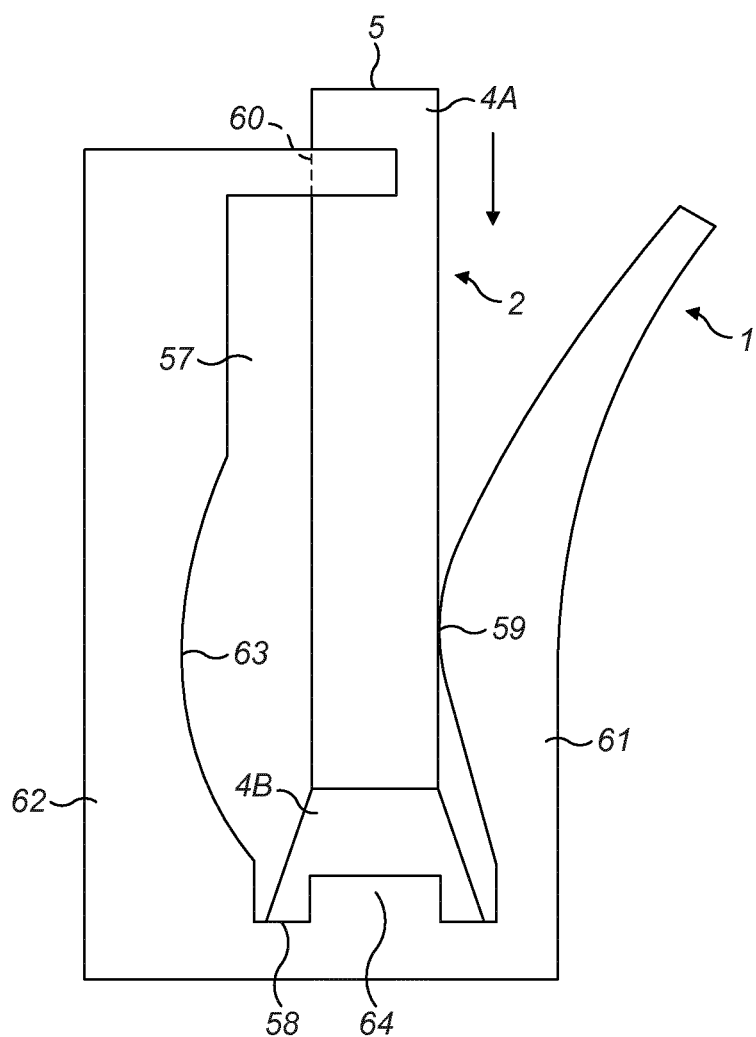
FIG. 8B shows an assembly nest according to the seventh embodiment of the disclosure.
Figure 8C:
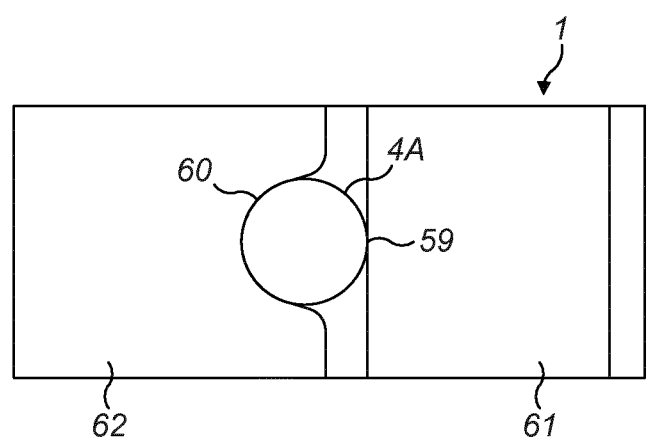
FIG. 8C shows an assembly nest according to the seventh embodiment of the disclosure.
Figure 10:
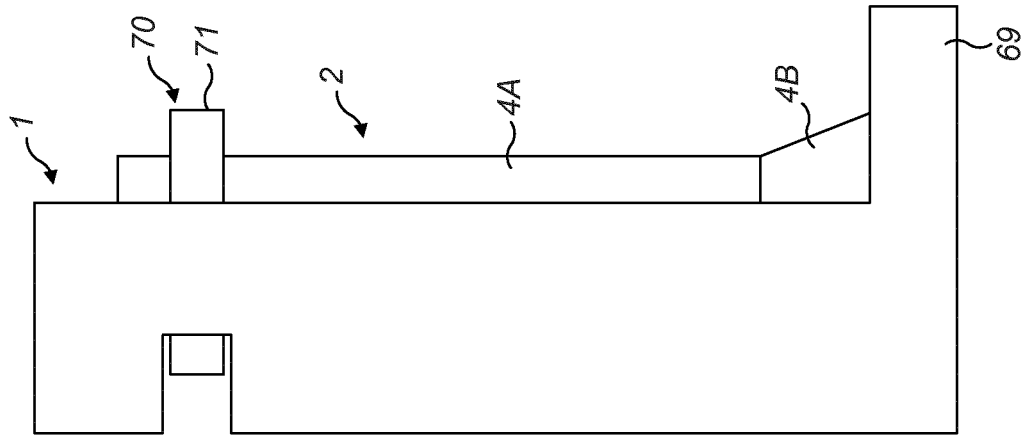
FIG. 10 shows an assembly nest according to the eighth embodiment of the disclosure in a locked position.
Figure 9:
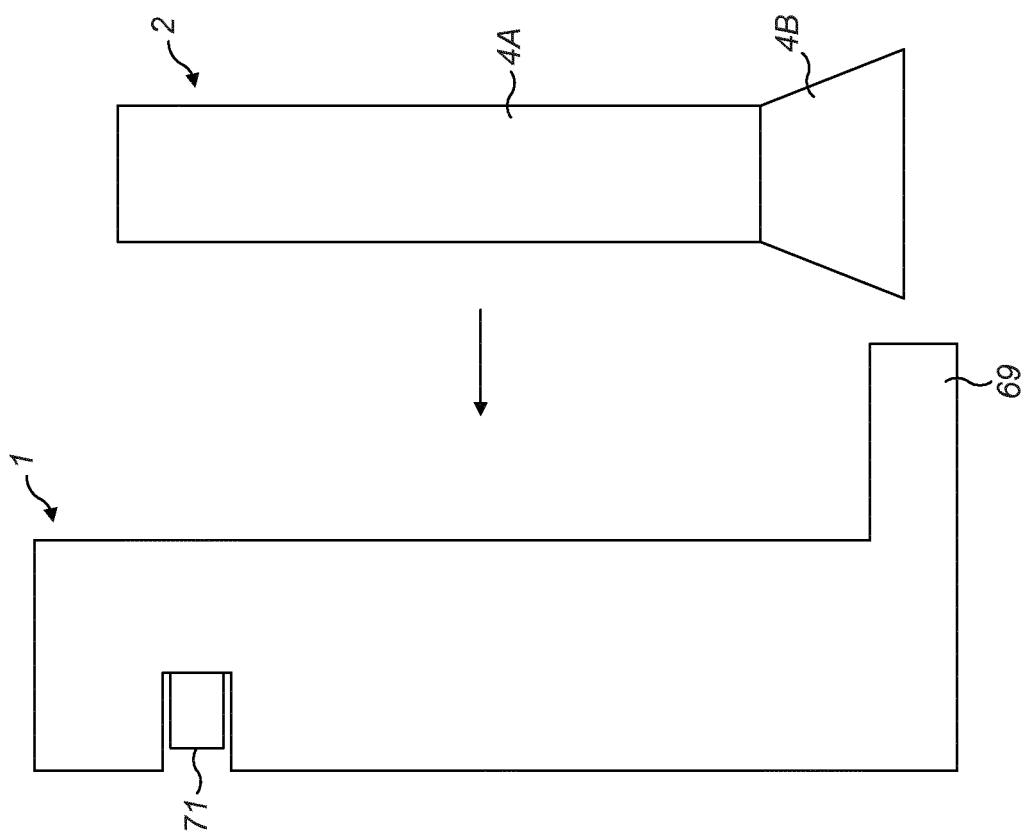
FIG. 9 shows an assembly nest according to a eighth embodiment of the disclosure in an unlocked position.

A seventh embodiment of the disclosure is shown in FIGS. 8A, 8B and 8C. The assembly nest 1 of the seventh embodiment includes an elongate receiving space 57 for receiving a sub assembly 2, a base surface 58, on which the cap 4B of the sub assembly 2 is mountable to orient it in the predetermined position, and first and second bearing surfaces 59, 60. The receiving space 57 is defined by a vertical projection of the base surface 58. Therefore, when the sub assembly 2 is mounted to the base surface 58 it is disposed within the receiving space 57, as shown in FIG. 8B. The bearing surfaces 59, 60 project into the receiving space and into contact with opposing sides of the tubular body 4A of a sub assembly 2 disposed in the receiving space 57.

The first and second bearing 59, 60 surfaces project, respectively, from first and second walls 61, 62 that upstand either side of the base surface 58. The bearing surfaces 59, 60 are spaced apart in a longitudinal direction of the receiving space 57 with the first bearing surface 59 located below the second 60, that is, closer to the base surface 58 of the receiving space 57. The first bearing surface 59 is preferably formed as a smooth curve in the profile of the first wall 61.

A recess 63 formed in the second wall 62 projects outwardly of the receiving space 57 to create space for the cap 4B to pass around the first bearing surface 59 and into contact with the base 58. The recess 63 is formed as a smooth curve in the profile of the second wall 62 such that the recess 63 and the first bearing surface 59 act to guide the cap 4B into the receiving space 57 and onto the base surface 58 when it is inserted therein.

The second, upper, bearing surface 60 forms a U shaped collar that extends around a portion of the tubular body 4A of the sub assembly 2 when it is received in the receiving space 57, as shown in FIG. 8C. This locates the proximal end 5 of the sub assembly in non-axial direction. Opposite the second bearing surface 60, an upper end of the first wall 61 extends away from the receiving space 57, following the curvature of the first bearing surface 59, so that the upper end of the first wall 61 and the first bearing surface 59 together form a mathematical spline in profile. The first wall 61 extends outwardly in this manner to create space for the cap 4B to pass between the second bearing surface 60 and the upper end of the first wall 61 and into the receiving space 57.

Two flange portions 64 upstand from either side of the base surface 58 between the first and second walls 61, 62. The first, lower, bearing surface 59 and the recess 63 are spaced from the base surface 58 in the longitudinal direction by respective bottom portions 65, 66 of the first and second walls 61, 62. The flange portions 64 and bottom portions 65, 66 of the first and second walls 61, 62 combine to fully constrain the cap 4B of the sub assembly 2 in the non-axial direction when the cap 4B is located on the base surface 58.

In use, an operator can insert the sub assembly 2 into the assembly nest 1 of the seventh embodiment by a composite movement in which the sub assembly 2 is orientated at an oblique angle to the base surface 58, somewhat parallel to the first wall 61 where it extends away from the receiving space 57, and moved in an axial direction to position the cap 4B into the recess 63 of the second wall 62, whereupon the sub assembly 2 can be rotated perpendicular to the base surface 58 and moved in an axial direction until the cap 4B abuts the base surface 58. With the sub assembly 2 so disposed in the receiving space, it is fully constrained in a non-axial direction so that only a corresponding composite movement in a direction opposite to insertion will enable it to be removed from the receiving space 57.

Figure 11:
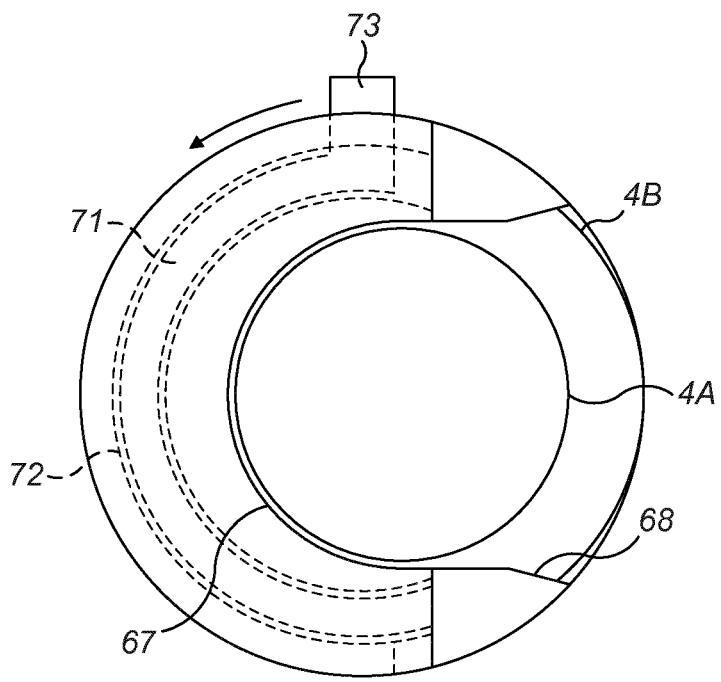
FIG. 11 shows an assembly nest according to the eighth embodiment of the disclosure in an unlocked position.
Figure 12:
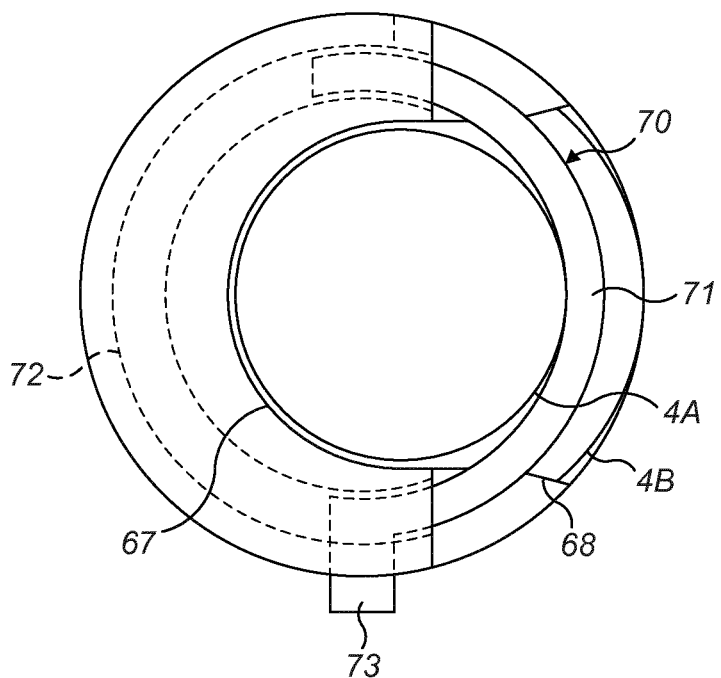
FIG. 12 shows an assembly nest according to the eighth embodiment of the disclosure in a locked position.

An eighth embodiment of the disclosure is shown in FIGS. 9 to 12. In this embodiment, the assembly nest 1 includes a semi cylindrical wall 67 which defines an elongate receiving space. The semi cylindrical wall 67 includes a longitudinal opening 68 along one side through which the sub assembly 2 can be inserted so that it is disposed in the receiving space, in which the tubular body 4A abuts the semi cylindrical wall 67; the cap abuts the lower end of the semi cylindrical wall 67; and a lower face of the cap 4B abuts a base 69 to orientate the sub assembly 2 in a predetermined position. This is best seen in FIGS. 11 and 12 in which the assembly nest 1 is shown from above.

A lower end of the semi cylindrical wall 67 tapers outwards to accommodate the cap 4B of the sub assembly 2 when it is received in the receiving space.

A clamp 70 is provided to retain the sub assembly 2 in the assembly nest 1 and to locate the sub assembly 2 in a non-axial direction. The clamp 70 moves relative to the semi cylindrical wall 67 between an open position, in which the longitudinal opening 68 is uncovered, and a closed position in which the clamp 70 abuts a sub assembly 2 inserted in the assembly nest 1 to secure it therein.

As best shown in FIGS. 11 and 12, the clamp 70 includes a slider 71 that describes a partial annulus. The slider 71 is disposed in an arcuate track 72 formed in an upper end of the semi cylindrical wall 67. The slider 71 rotates about its axis along the track 72 between the open and closed positions. In the open position the slider 71 is disposed substantially within the track 72 so that it does not obstruct the opening 68. In the closed position, the slider 71 is disposed partially within the track 72 with the remainder of the slider 71 disposed across the opening 68. A grip 73 extends from a slot in a rear face of the cylindrical wall 67 to allow the slider 71 to be moved along the track 72 between the open and closed positions.

In use, an operator can insert the sub assembly 2 into the assembly nest 1 by moving the sub assembly 2 in a direction perpendicular to its axis through the longitudinal opening 68 in the semi cylindrical wall 67. With the tubular body 4A located against the semi cylindrical wall 67, the slider 71 is moved into the closed positon so that an inside edge of the slider 71 abuts the tubular body 4A to prevent it moving in a non-axial direction.

Figure 13A:
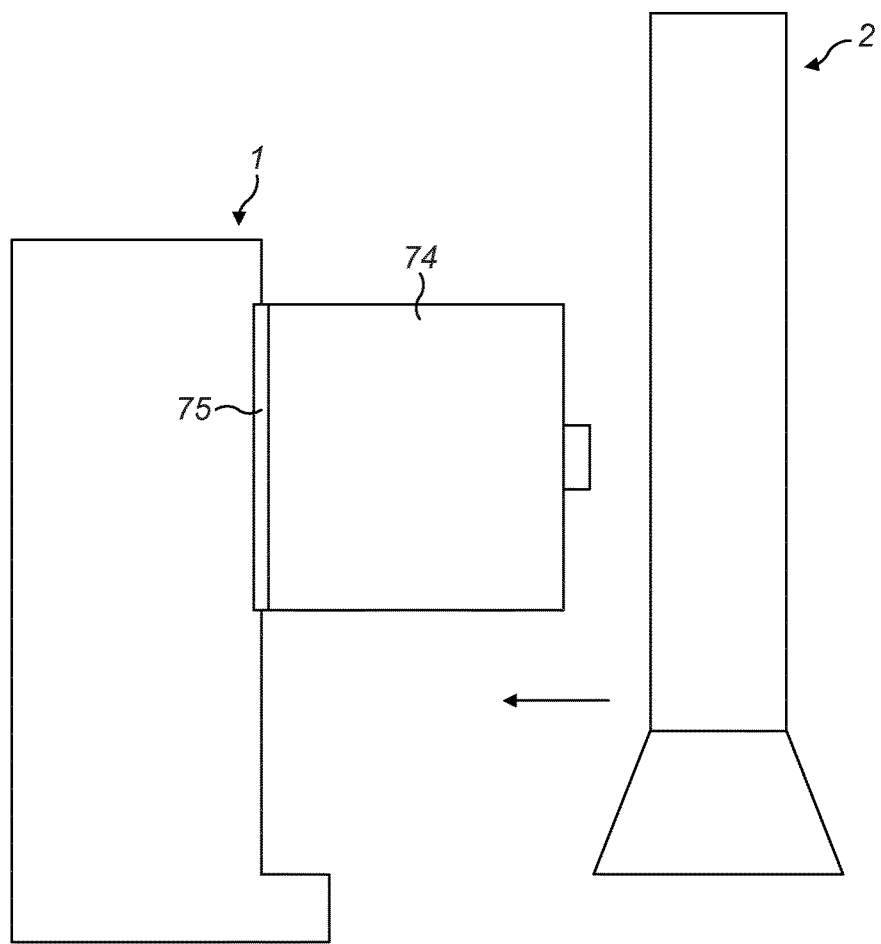
FIG. 13A shows an assembly nest according to an ninth embodiment of the disclosure in an unlocked position.
Figure 13B:
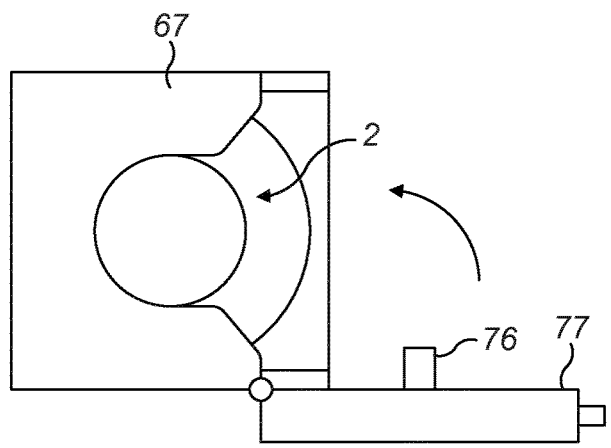
FIG. 13B shows an assembly nest according to the ninth embodiment of the disclosure in an unlocked position.

In a ninth embodiment, shown in FIGS. 13A and 13B, in which like features retain the same reference numbers, the slider is omitted and instead a panel 74 is provided attached to the wall 67 of the by a hinge 75 along one edge of the panel 74. The panel 74 hinges between an open position, in which the sub assembly 2 can be inserted in through the longitudinal opening 68 as described above, and a closed position in which the panel 74 extends across the longitudinal opening 68 to retain a sub assembly 2 mounted in the assembly nest. The panel 74 can include a fixation element 76 that extends from a rear face 77 of the panel 74 and into contact with the tubular body 4A of a sub assembly 2 received in the assembly nest 1. Therefore the sub assembly 2 is located in a non-axial direction. The panel 74 can be held in the closed position by a locking mechanism (not shown), for example a latch which engages a sprung catch provided in the semi cylindrical wall 67.

The hinge 75 between the panel 74 and the semi cylindrical wall 67 can include a spring to bias the panel 74 into the open position.

Figure 14B:
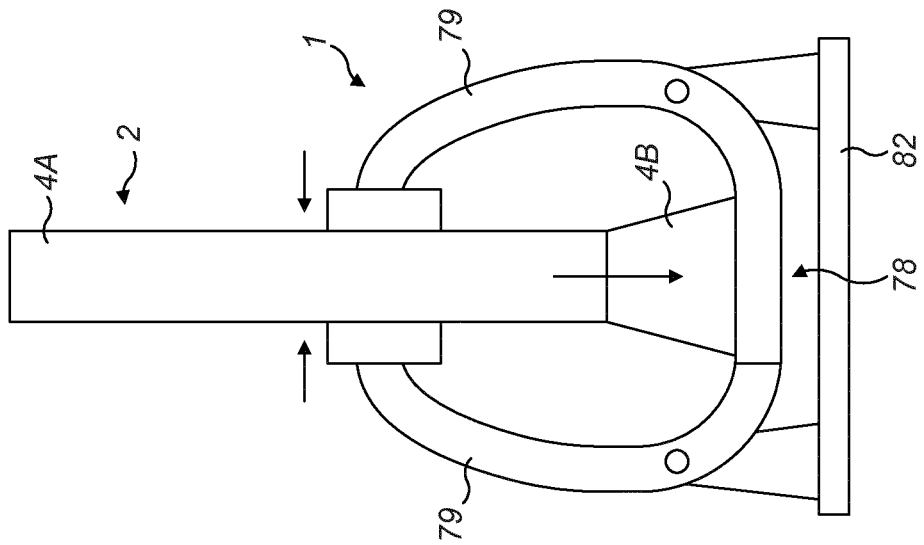
FIG. 14B shows an assembly nest according to the tenth embodiment of the disclosure in a locked position.
Figure 14A:
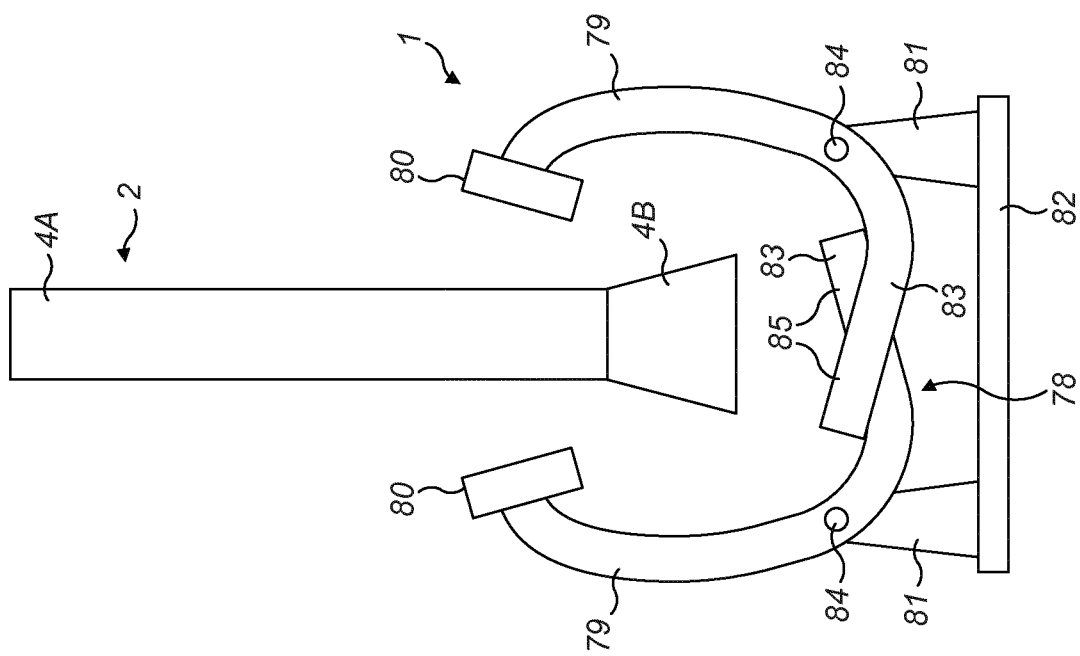
FIG. 14A shows an assembly nest according to a tenth embodiment of the disclosure in an unlocked position.
Figure 15:
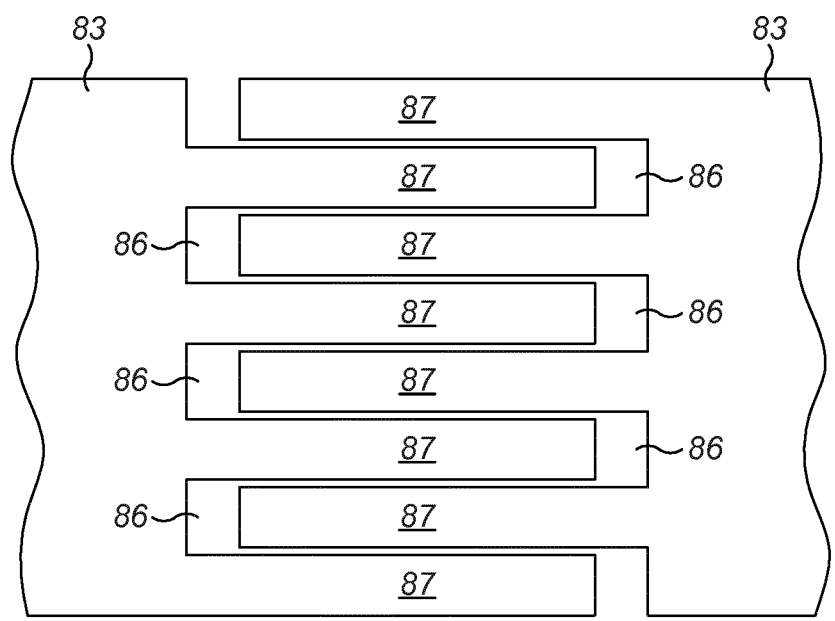
FIG. 15 shows part of an assembly nest according to the tenth embodiment of the disclosure.

In a tenth embodiment of the disclosure shown in FIGS. 14A, 14B and 15 the assembly nest 1 includes a mount 78 against which the cap 4B of the sub assembly 2 is mountable to orientate it in a predetermined position; and a clamping arm that extends upwardly from the mount 78 and is moveable into a locked position in response to displacement of the mount 78 in which a clamping surface 80 of the clamping arm abuts the tubular body 4A of a sub assembly 2 mounted to the mount 78.

In the illustrated embodiment, two clamping arms 79 are provided. Each clamping arm 79 is mounted to a bracket 81 upstanding from a base 82 of the assembly nest by a hinge 84. The mount 78 includes two individual mounting parts 83 that are each integrally formed with a respective clamping arm 79. Each of the mounting parts 83 extend generally perpendicularly to from a lower end of their respective clamping arm 79; the clamping arms 79 and the mounting parts 83 extending either side of the hinge 84.

The mounting parts 83 extend towards each other and into overlapping relation. Specifically, each mounting part 83 includes open ended slots 86 (best seen in FIG. 15) that extend through the mounting part 83 and are regularly spaced along its width. The portions of the mounting parts 83 between the slots 86 will herein be referred to as fingers 87. The slots 86 allow the fingers 87 of the opposed mounting parts 83 to move in between each other. When the clamping arms 79 are arranged in the locked position, the fingers 87 of each mounting part 83 are aligned so that, combined, they form a flat surface which is perpendicular to the clamping surfaces 80. Consequently, when the cap 4B of a sub assembly 2 is disposed on the mount 78, and the clamping arms 79 are in the locked position so that the mounting parts 83 of the mount 78 form a flat surface, the clamping surfaces 80 abut opposing sides of the tubular body 4A of the sub assembly.

In use, the clamping arms 79 are initially disposed in an unlocked position, in which the clamping surfaces 80 are spaced apart. In the unlocked position, the mounting parts 83 are both tilted upward such that they are arranged at an oblique angle relative to each other. An operator can then place the cap 4B of a sub assembly 2 down against the mounting parts 83 before pressing the sub assembly 2 downwards to simultaneously displace the mounting parts 83 and the clamping arms 79 into a locked position in which the mounting parts 83 are moved into alignment to form a flat surface and the clamping surfaces 80 are moved into abutting relation with opposite sides of the tubular body 4A of the sub assembly 2. With the clamping arms 79 disposed in the locked positon, the clamping surfaces 80 locate the sub assembly 2 in a non-axial direction.

Figure 17:
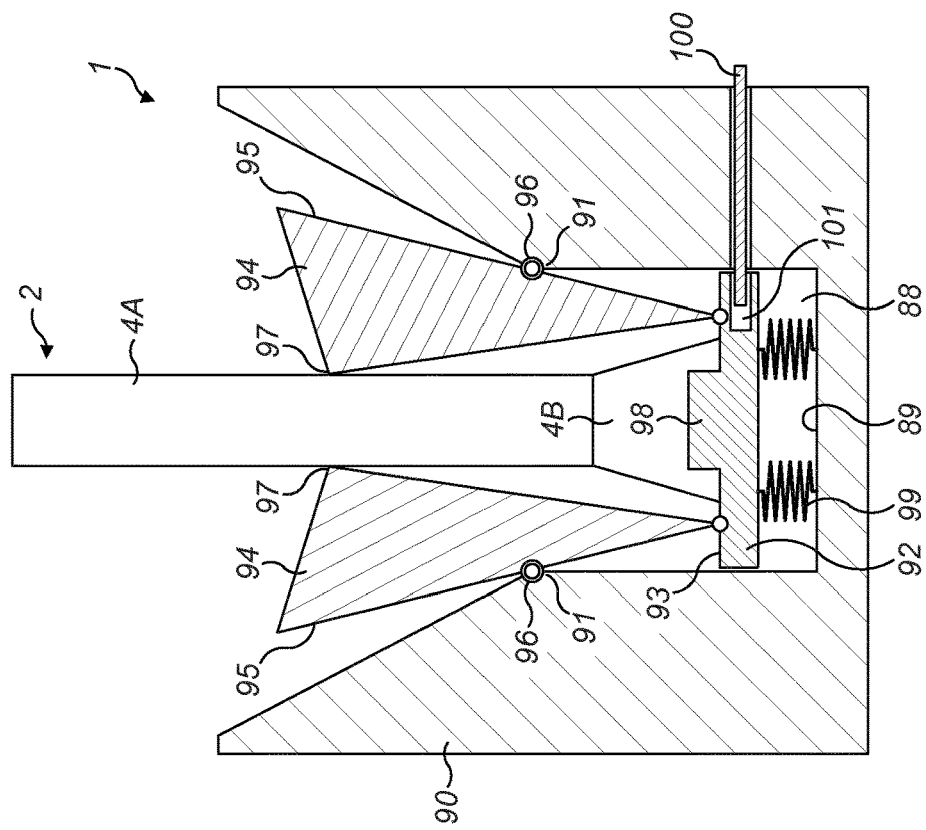
FIG. 17 shows an assembly nest according to the eleventh embodiment of the disclosure in a locked position.
Figure 16:
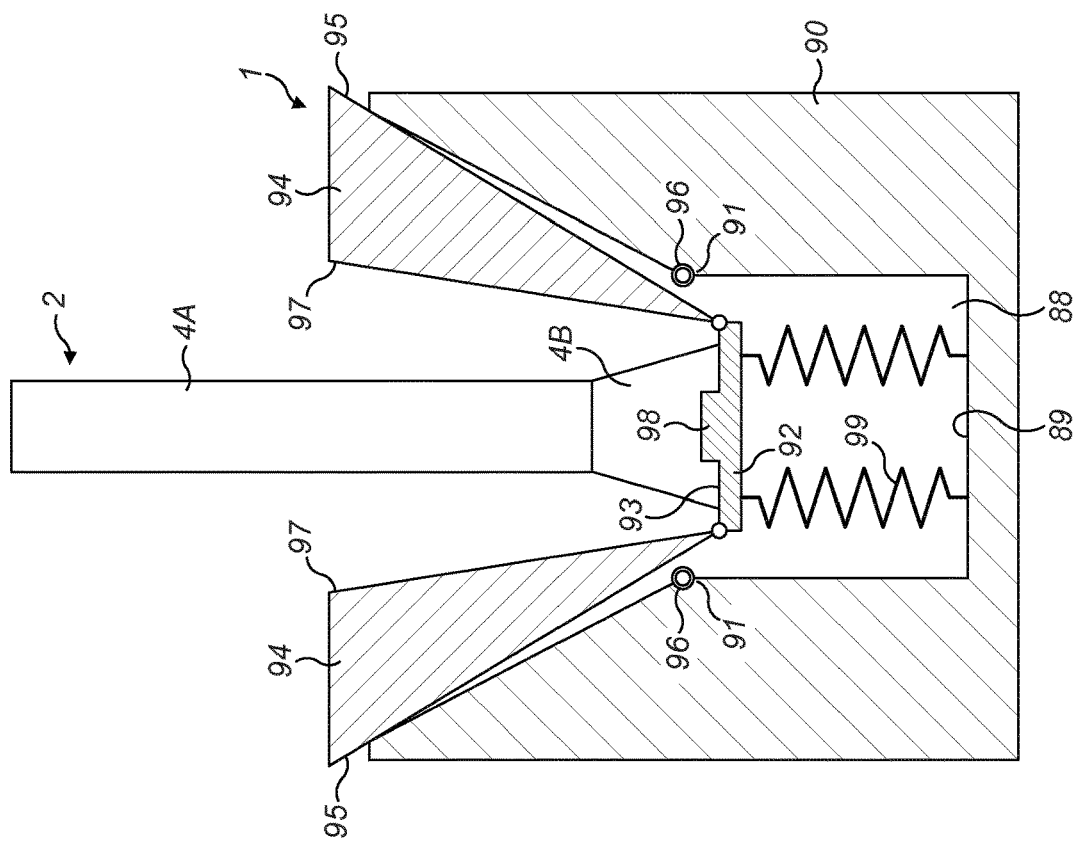
FIG. 16 shows an assembly nest according to a eleventh embodiment of the disclosure in an unlocked position.

An eleventh embodiment of the disclosure is shown in FIGS. 16 and 17. In this embodiment, the assembly nest includes 1 a receiving space 88 defined by a vertical projection of a base surface 89 of the receiving space 88. A wall upstands 90 perpendicularly around the receiving space 88 and terminates at an upper edge 91. In this embodiment a mount 92 is moveably disposed in the receiving space 88 in a longitudinal direction of the receiving space 88. The mount 92 provides a mounting surface 93 arranged perpendicular to the longitudinal direction so that the cap 4B of a sub assembly 2 can be placed onto mounting surface 93.

Clamping arms 94 are hingedly attached either side of the mounting surface 93 and include an extended straight edge 95 that rests against the upper edge 91 of the wall. Roller bearings 96 can be provided along the upper edge 91 of the wall 90 to allow the straight edge 91 of the clamping arms 94 to easily slide over the upper edge 91 as will be explained in more detail below.

In an unlocked position, shown in FIG. 16, the mount 92 is disposed at an upper end of the receiving space 88, that is, it is spaced from the base 89. With the mount 92 disposed in this position, the clamping arms 94 extend outwards from the mount 92, away from the receiving space 88. A clamping surface 97 projects from an upper end of the clamping arm 94 toward the receiving space 88.

In use, an operator can place the cap 4B of a sub assembly 2 onto the mount 92, before moving the sub assembly 2 downwards in an axial direction to cause the clamping arms 94 to pivot around the upper edge 91 of the wall 90, towards the tubular body 4A and into the locked position. In the locked position, the clamping surfaces 97 abut opposite sides of the tubular body 4A to locate the tubular body 4A in a non-axial direction.

To locate the cap 4B, the mount includes flanges 98 that upstand from the mount 93 between the clamping arms 94. When the sub assembly 2 is inserted into the assembly nest 1, the cap 4B abuts the flanges 98 are closely spaced to the cap 4B to locate the cap 4B in a non-axial direction.

A compression spring 99 can be provided between the base 89 and the mount 92 to bias the mount 92 into the unlocked position. A locking pin 100 can also be provided to retain the mount 92 in the locked position. The locking pin 100 extends through the wall 90 and into a groove 101 in the side of the mount 92 so that when the mount 92 is in the locked position and the groove 101 and the pin 100 are aligned, the pin 100 can be moved across and into the groove 101 to prevent the mount 92 from moving in a longitudinal direction of the receiving space 88.

Figure 19:
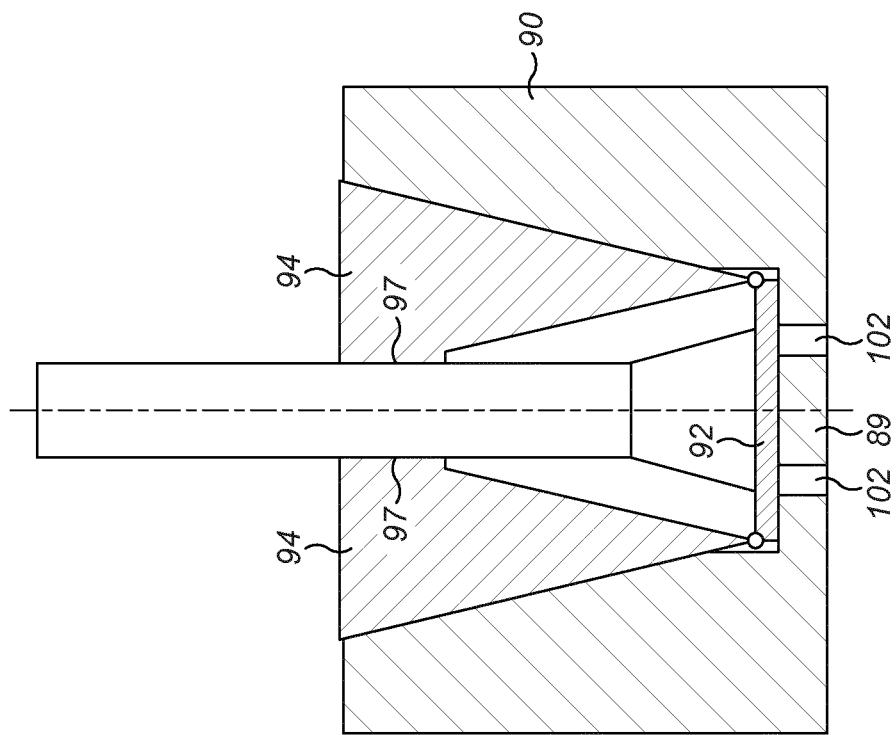
FIG. 19 shows an assembly nest according to the twelfth embodiment of the disclosure in a locked position.
Figure 18:
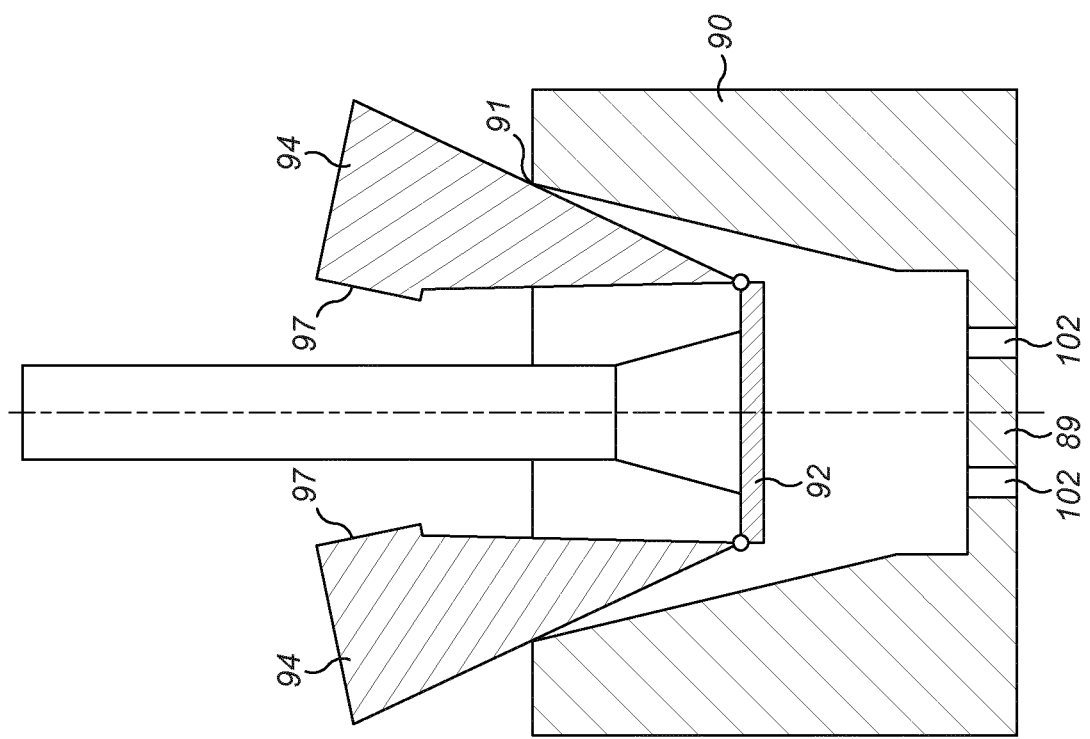
FIG. 18 shows an assembly nest according to a twelfth embodiment of the disclosure in an unlocked position.

In a twelfth embodiment, shown in FIGS. 18 and 19, in which like features retain the same reference numbers, openings 102 are provided in the base 89 to allow for the passage of fluid into the receiving space 88. Therefore, air can pass through the openings 102 as the mount moves up and down the receiving space 88 to prevent the formation of a pressure difference between upper and lower surfaces of the mount 92. Such a pressure difference would cause a resistance to movement of the mount 92. For example, when the mount 92 is moved downwards into the locked position, air can pass out through the openings 102. Likewise, when the mount 92 is moved up and into the unlocked position, air can pass in through the openings 102.

Figure 21:
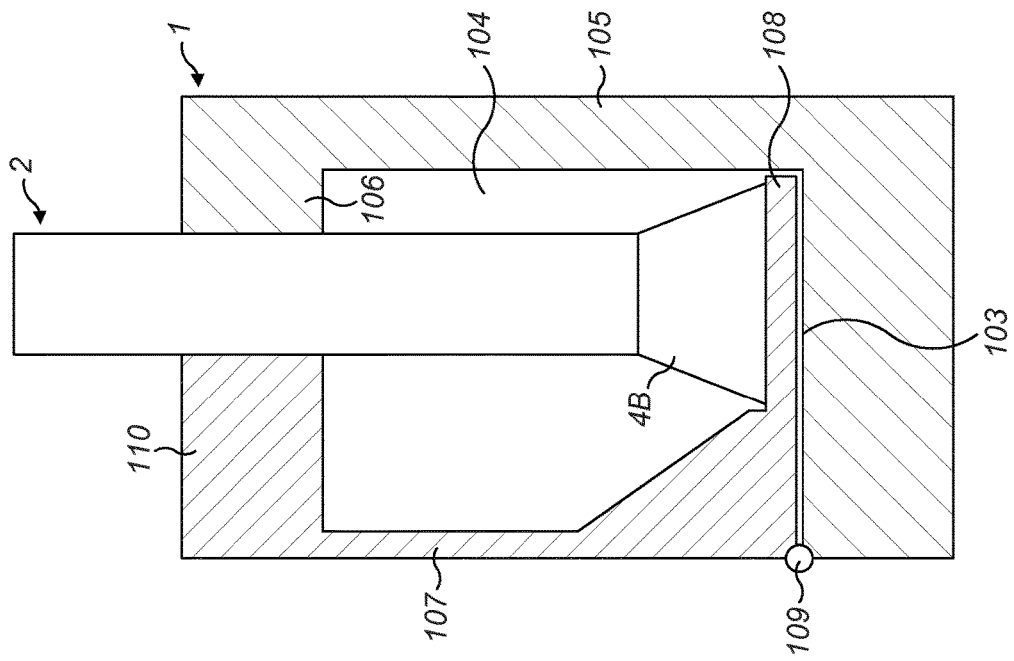
FIG. 21 shows an assembly nest according to the thirteenth embodiment of the disclosure in a locked position.
Figure 20:
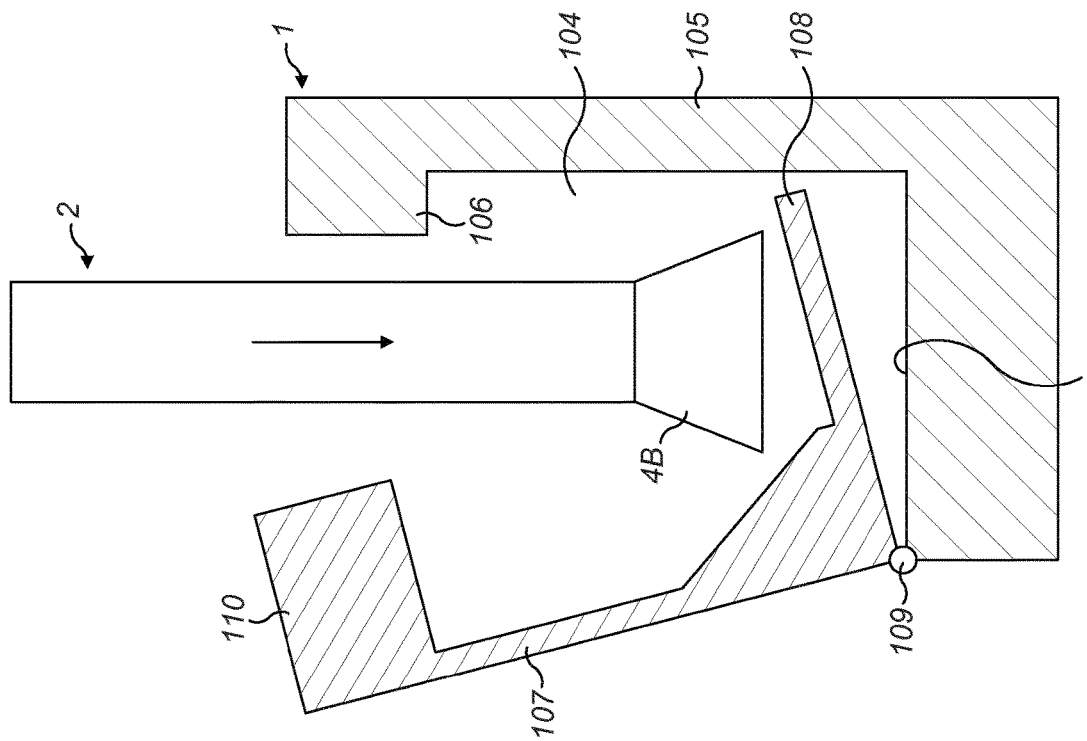
FIG. 20 shows an assembly nest according to a thirteenth embodiment of the disclosure in an unlocked position.

In a thirteenth embodiment of the disclosure, shown in FIGS. 20 and 21, the assembly nest 1 includes a base surface 103 and a receiving space 104 defined by a vertical projection of the base surface 103. A support 105 upstands from one side of the base surface 103 and includes an alignment element 106 that projects into the receiving space 104 from an upper end of the support 105. A clamping arm 107 is mounted to the base surface 103 opposite the support 105 by a hinge 109 and is moveable between a locked position, in which the clamping arm 107 extends upwards perpendicular to the base surface 103, and an unlocked position in which the clamping arm 107 extends at an oblique angle to the base surface 103, outwardly of the receiving space 104. The locked position illustrated in FIG. 21 and the unlocked position in FIG. 20.

The clamping arm 107 is integrally formed with a mount 108. The clamping arm 107 and the mount 108 are arranged perpendicular to each other and extend either side of the hinge 109 such that, when the clamping arm 107 is in the locked position, the mount 108 rests on the base surface 103. Conversely, when the clamping arm 107 is in the unlocked position, the mount is angled upward from the base surface 103.

A fixation element 110 extends from an upper end of the clamping arm 107 opposite the alignment element 106. When the clamping arm 107 is in the unlocked position, the fixation element 107 is spaced from the alignment element 106 to allow the cap 4B of a sub assembly 2 to be inserted into the assembly nest 1.

In use, the clamping arm 107 is initially in the unlocked position so that an operator can insert the sub assembly 2 into the assembly nest 1 between the fixation and alignment elements 110, 106. The cap 4B of the sub assembly 2 is placed on the mount 108 and pushed downwards to cause the mount 108 to move against the base surface 103 and the clamping arm 107 to move into the locked position, whereupon the tubular body 4A of the sub assembly 2 is clamped between clamping surfaces 131 of fixation element 110 and the alignment element 106 to hold the sub assembly 2 in a predetermined position.

Figure 23:
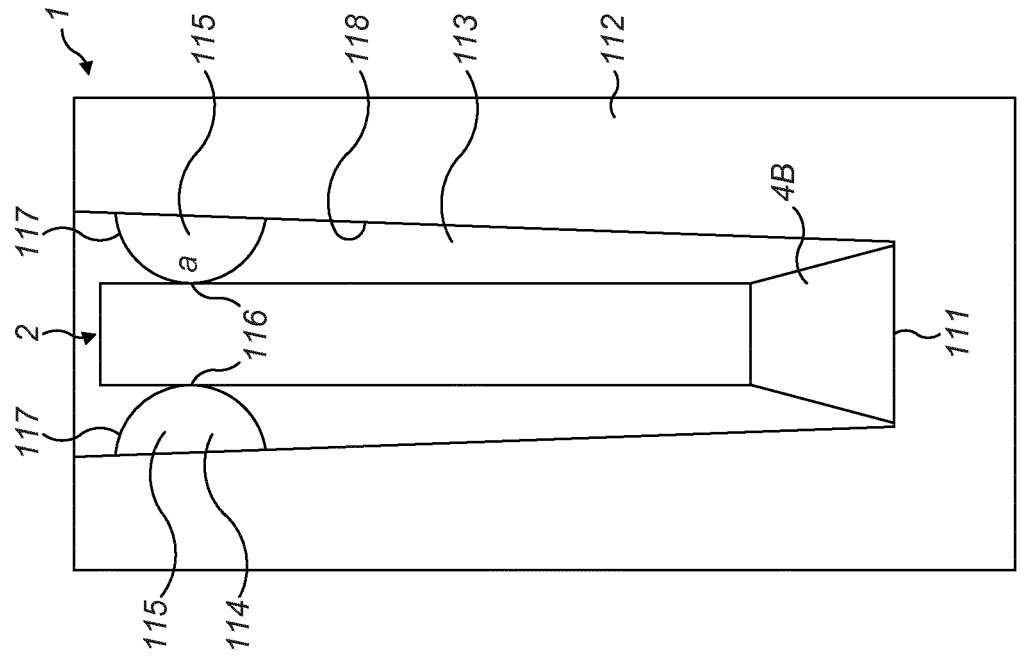
FIG. 23 shows an assembly nest according to the fourteenth embodiment of the disclosure in a locked position.
Figure 22:
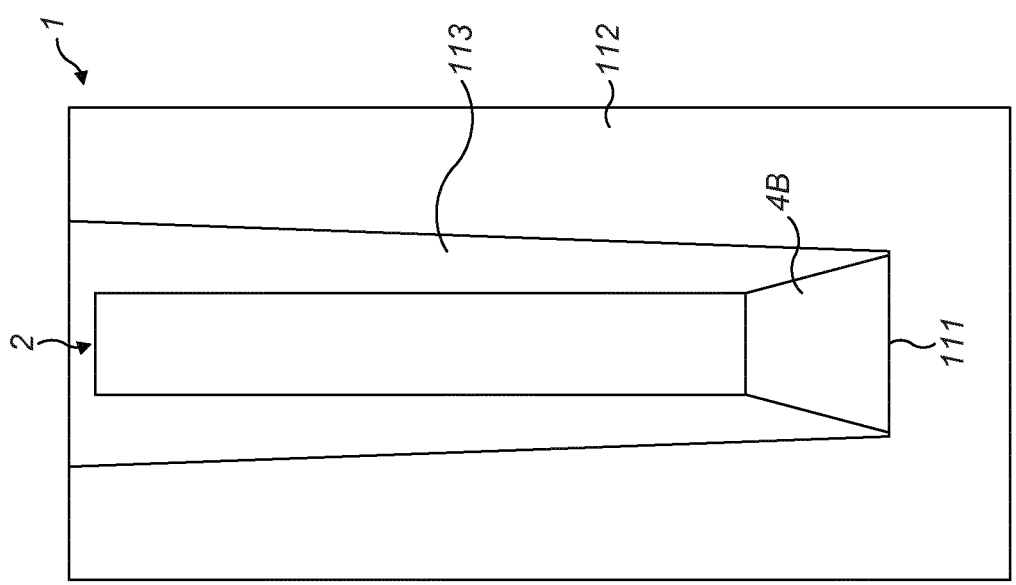
FIG. 22 shows an assembly nest according to a fourteenth embodiment of the disclosure in an unlocked position.

In a fourteenth embodiment, shown in FIGS. 22 and 23, the assembly nest 1 includes a base surface 111 against which the cap 4B of a sub assembly 2 can be mounted to orient it in a predetermined position and a wall 112 that upstands around the base surface 111 to define a receiving space 113 in which the sub assembly 2 is disposed when the cap 4B is mounted to the base surface 111. A clamping mechanism 114 is provided to clamp a sub assembly 2 disposed in the receiving space 113.

The clamping mechanism 114 includes a reservoir 115 and a clamping surface 116. Fluid can be pumped into the reservoir 115 to displace the clamping surface 116 into contact with the tubular body 4A of a sub assembly 2 mounted to the base surface 111.

For example, as shown in FIG. 23, the reservoir 115 can include a flexible membrane 117 mounted to an inside face 118 of the wall 112 of the assembly nest 1. A pump not shown is fluidly connected, and sealed to, the flexible membrane 117. Therefore, when the pump is activated, air is pumped into the flexible membrane 117 to cause it to inflate. In such an embodiment, the clamping surface 116 is an exterior surface of the flexible membrane 117 so that, when it is inflated, the exterior surface moves into contact with the tubular body 4A of the sub assembly 2 mounted to the base surface 111. In order to effect clamping of the tubular body 4A, two flexible membranes 117 are provided in opposite inside faces 118 of the wall 112 such that, when inflated, the respective clamping surfaces 116 abut opposite sides of the tubular body 4A of the sub assembly 2 mounted to the base surface 111.

In another unillustrated embodiment, the clamping mechanism can instead include a cylinder, which serves as the reservoir, and a piston moveable within the cylinder, an end face of which serves as the clamping surface. Therefore the clamping mechanism takes the form of a conventional pneumatic actuator. In such embodiments, two pneumatic actuators are provided either side of the tubular body 4A of a sub assembly 2 mounted to the base 111 and extend from the inside face 118 of the wall 112 in response to a fluid being pumped into the cylinder to clamp the tubular body 4A between clamping faces of the piston.

In use, an operator can insert a sub assembly 2 down into the receiving space 113 so that the cap 4B abuts the base surface 111, whereupon the pump is activated to cause the clamping surfaces 116 of the clamping mechanism 114 to move into contact with either side of the tubular body 4A. Therefore the sub assembly 2 is located in a predetermined position and held both in an axial and non-axial direction by frictional engagement of the tubular body by the clamping surfaces 116.

Figure 25:
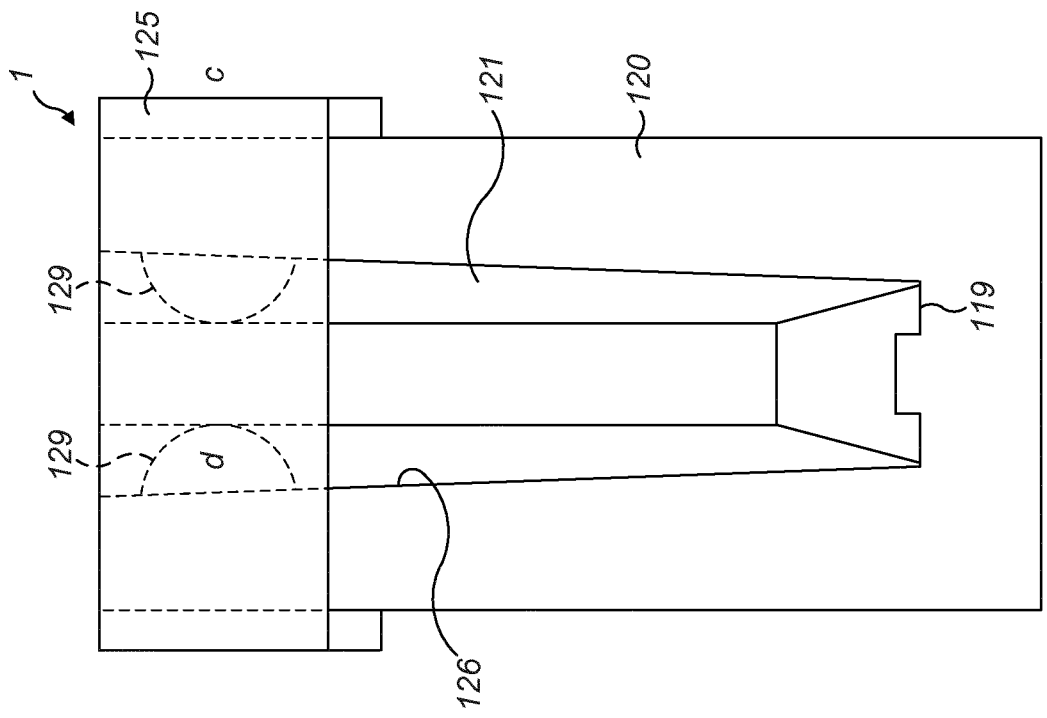
FIG. 25 shows an assembly nest according to the fifteenth embodiment of the disclosure in a locked position.
Figure 24:
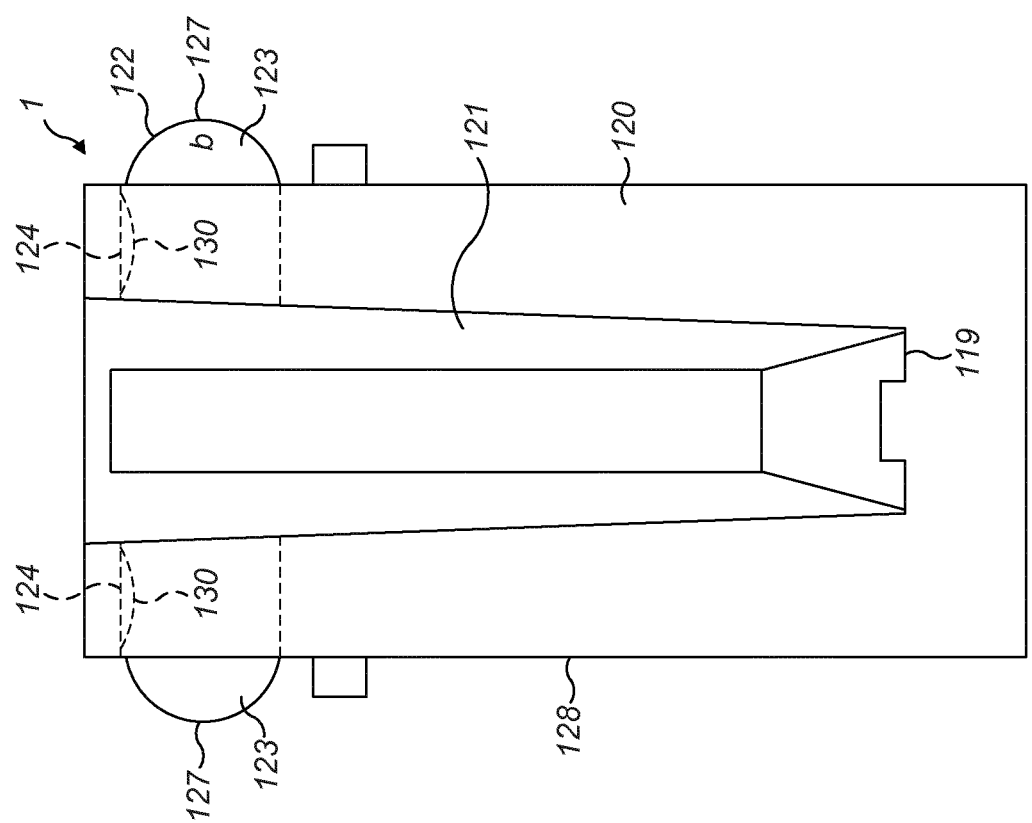
FIG. 24 shows an assembly nest according to a fifteenth embodiment of the disclosure in an unlocked position.

In a fifteenth embodiment of the disclosure shown in FIGS. 24 and 25 the assembly nest 1 includes a base surface 119 against which the cap 4B of a sub assembly 2 can be mounted to orient it in a predetermined position and a wall 120 that upstands around the base surface 119 to define a receiving space 121 in which the sub assembly 2 is disposed when the cap 4B is mounted to the base surface 119. A clamping mechanism 122 is provided to clamp a sub assembly 2 disposed in the receiving space 121.

The clamping mechanism 122 includes a clamp 123 disposed in a track 124 formed through an upper end of the wall 120. As shown in FIG. 25, the clamp 123 is displaceable along the track 124 in response to a locking collar 125 being placed over the upper end of the wall 120 into a locked position in which the clamp 123 protrudes from an inner surface 126 of the wall 120 and into engagement with the tubular body 4A of a sub assembly 2 mounted to the base surface 119.

The clamp includes a curved outer face 127 that protrudes from an outer surface 128 of the wall 120 when the clamp 123 is in an unlocked position.

In order to effect clamping of the tubular body 4A, two clamping mechanisms 122 are provided opposite each other such that, when the locking collar 125 is placed over the upper end of the wall 120, the respective clamps 122 are displaced to abut opposite sides of the tubular body 4A of the sub assembly 2 mounted to the base surface 119.

In use, an operator can insert a sub assembly 2 down into the receiving space 121 so that the cap 4B abuts the base surface 119, whereupon the locking collar 125 can be placed over the upper end of the wall 120. The locking collar 125 is a closely spaced fit to the upper end of the wall 120 so that it comes into contact with the curved outer faces 127 of the two clamps 123. The shape of the curved outer faces 127 causes them to be displaced inwards as a result of the downward movement of the locking collar 125, and into contact with the tubular body 4A of the sub assembly 2. Therefore the sub assembly 2 is located both in an axial and non-axial direction by frictional engagement of the tubular body 4A with the clamps 123.

The clamping mechanism 122 can further include a curved inner surface 129 so that it is displaced in the opposite direction by removing the sub assembly 2 from the receiving space 121. Specifically, as the sub assembly 2 is removed from the receiving space 121, the cap 4B comes into contact with the clamp 123 so that upwards movement of the sub assembly 2 moves the clamp 123 back into the unlocked position.

Optionally a leaf spring 130 is provided in each of the tracks 124, the leaf spring 130 being bowed outwards to create a restriction halfway along the track 124. Therefore, movement of the clamp 123 along the track 124 compresses the leaf spring 130 such that the clamp 123 is always urged away from the center of the track 124 and into one of the locked or unlocked positions.

Those of skill in the art will understand that modifications (additions and/or removals) of various components of the substances, formulations, apparatuses, methods, systems and embodiments described herein can be made without departing from the full scope and spirit of the present disclosure, which encompass such modifications and any and all equivalents thereof.

The invention claimed is:

1. An assembly nest for transporting a sub assembly of a drug delivery device on an automated production line, wherein the sub assembly comprises a tubular body and a cap that is wider than the tubular body, the assembly nest comprising:
   a base against which the sub assembly of the drug delivery device is mountable to orientate the sub assembly in a predetermined position; and
   a locking mechanism having a resilient member to urge the locking mechanism into at least one of:
      an unlocked position, in which the sub assembly of the drug delivery device can be mounted to the base; or
      a locked position, in which the locking mechanism engages the sub assembly when it is mounted to the base to retain it in the predetermined position on the base;
   wherein the locking mechanism comprises a locking pin having a gripping end that abuts the sub assembly when the sub assembly is mounted on the base and when the locking mechanism is in the locked position and is spaced from the sub assembly when the locking mechanism is in the unlocked position;
   and wherein the resilient member comprises a coil spring arranged about the locking pin and arranged to urge the gripping end against the sub assembly when the sub assembly is mounted to the base.

2. The assembly nest according to claim 1, comprising two symmetrically opposed locking pins.

3. An assembly nest for transporting a sub assembly of a drug delivery device on an automated production line, wherein the sub assembly comprises a tubular body and a cap that is wider than the tubular body, the assembly nest comprising:
   a base against which the sub assembly of the drug delivery device is mountable to orientate the sub assembly in a predetermined position; and
   a locking mechanism having a resilient member to urge the locking mechanism into at least one of:
      an unlocked position, in which the sub assembly of the drug delivery device can be mounted to the base; or
      a locked position, in which the locking mechanism engages the sub assembly when it is mounted to the base to retain it in its predetermined position on the base;
   wherein the assembly nest further comprises an upper part and a lower part that are combinable with each other, wherein the lower part comprises the base, and wherein the upper part comprises the locking mechanism, the locking mechanism comprising resilient arms that depend from the upper part and that extend into contact with the sub assembly when it is mounted to the base and when the upper and lower parts are combined.

4. The assembly nest according to claim 3, wherein the lower part comprises a wall that upstands around the base to define a receiving space into which the sub assembly of the drug delivery device is inserted when the sub assembly is mounted to the base, and wherein the wall comprises a protrusion that extends into the receiving space and is arranged so as to displace the resilient arms toward the sub assembly mounted to the base when the upper and lower parts are combined.

5. An assembly nest for transporting a sub assembly of a drug delivery device on an automated production line, wherein the sub assembly comprises a tubular body and a cap that is wider than the tubular body, the assembly nest comprising:
   a base against which the sub assembly of the drug delivery device is mountable to orientate the sub assembly in a predetermined position; and
   a locking mechanism having a resilient member to urge the locking mechanism into at least one of:
      an unlocked position, in which the sub assembly of the drug delivery device can be mounted to the base; or
      a locked position, in which the locking mechanism engages the sub assembly when it is mounted to the base to retain it in the predetermined position on the base;
   wherein the locking mechanism comprises at least two resilient arms that extend either side of the base and a locking ring positionable over ends of the at least two resilient arms to retain the locking mechanism in the locked position, the at least two resilient arms being arranged so that when the locking mechanism is in the unlocked position, the at least two resilient arms extend outward of a space defined by a vertical projection of the base, the locking mechanism further comprising engaging portions that depend from upper edges of the at least two resilient arms and extend into said space when the locking mechanism is in the locked position.

6. The assembly nest according to claim 5, wherein the locking ring is slideably arranged around the at least two resilient arms, and wherein sliding the locking ring along a length of the at least two resilient arms into the locked position causes the at least two resilient arms to move toward each other so as to engage the sub assembly when it is mounted on the base.

7. An assembly nest for transporting a sub assembly of a drug delivery device on an automated production line, wherein the sub assembly comprises a tubular body and a cap that is wider than the tubular body, the assembly nest comprising:
   a base against which the sub assembly of the drug delivery device is mountable to orientate the sub assembly in a predetermined position; and
   a locking mechanism having a resilient member to urge the locking mechanism into at least one of:
      an unlocked position, in which the sub assembly of the drug delivery device can be mounted to the base; or
      a locked position, in which the locking mechanism engages the sub assembly when it is mounted on the base to retain it in the predetermined position on the base;

the assembly nest further comprising:
an elongate receiving space for receiving the sub assembly defined by a vertical projection of an upper surface of the base; and
a support upstanding perpendicularly from the base having an alignment element at an upper end thereof that projects into the receiving space, such that, when the sub assembly is received in the receiving space, the cap abuts the base and the alignment element abuts the tubular body;
wherein the locking mechanism extends from the base opposite the support and comprises a fixation element that projects into the receiving space when the locking mechanism is in the locked position to clamp the tubular body of the sub assembly received therein between the alignment element and the fixation element.

8. The assembly nest according to claim 7, wherein the locking mechanism is hingedly attached to the base, and wherein a push rod extends through the base and is mechanically coupled to the locking mechanism such that movement of the push rod effects movement of the locking mechanism between the locked and unlocked positions.

9. An assembly nest for transporting a sub assembly of a drug delivery device on an automated production line, wherein the sub assembly comprises a tubular body and a cap that is wider than the tubular body, the assembly nest comprising:
an elongate receiving space for receiving the sub assembly, a base surface and at least two bearing surfaces, wherein the elongate receiving space is defined by a vertical projection of the base surface, the bearing surfaces projecting inwardly into an interior of the vertical projection of the base surface and into the receiving space such that when the sub assembly is received in the receiving space, the cap abuts the base surface and the bearing surfaces abut opposing sides of the tubular body, wherein the bearing surfaces are spaced apart in a longitudinal direction of the receiving space and wherein a recess is provided opposite a lower bearing surface, the recess projecting outwardly away from the interior of the vertical projection of the base surface and away from the receiving space.

10. The assembly nest according to claim 9, wherein an upper bearing surface forms a U shaped collar that extends around a portion of the tubular body when the sub assembly is received in the receiving space; and/or
wherein the lower bearing surface and the recess are spaced from the base surface in the longitudinal direction.

11. An assembly nest for transporting a sub assembly of a drug delivery device on an automated production line, wherein the sub assembly comprises a tubular body and a cap that is wider than the tubular body, the assembly nest comprising:
an elongate receiving space defined by a semi cylindrical wall having a longitudinal opening along one side in which the sub assembly can be inserted to orientate the sub assembly in a predetermined position; and
a clamp that moves relative to the receiving space between an open position, in which the longitudinal opening is uncovered, and a closed position in which the clamp partially covers the longitudinal opening and abuts the sub assembly inserted in the receiving space to secure it therein.

12. The assembly nest according to claim 11, wherein the receiving space comprises a base against which the cap of the sub assembly is mountable.

13. The assembly nest according to claim 11, wherein the clamp comprises a panel attached to the semi cylindrical wall by a hinge, and wherein in the closed position, the panel extends across the longitudinal opening.

14. The assembly nest according to claim 11, wherein the clamp comprises a slider that defines a partial annulus, the slider being disposed in an arcuate track formed in an upper end of the semi cylindrical wall, and wherein the slider is slideable along the arcuate track between the open and closed positions.

15. An assembly nest for transporting a sub assembly of a drug delivery device on an automated production line, wherein the sub assembly comprises a tubular body and a cap that is wider than the tubular body, the assembly nest comprising:
a base against which the cap of the sub assembly is mountable to orientate the sub assembly in a predetermined position;
a wall that upstands around the base; and
a clamping mechanism to clamp the tubular body of the sub assembly when the cap is mounted on the base, the clamping mechanism comprising a clamp disposed in a track formed through an upper end of the wall, the clamp being displaceable along the track in response to a locking collar being placed around an external surface of the upper end of the wall between an unlocked position, in which it protrudes from an outer surface of the wall, and a locked position in which it protrudes from an inner surface of the wall and into contact with the tubular body of the sub assembly when the cap is mounted on the base.

* * * * *